US009821073B2

(12) United States Patent
Willemsen et al.

(10) Patent No.: US 9,821,073 B2
(45) Date of Patent: *Nov. 21, 2017

(54) POLYPEPTIDE THAT BINDS ABERRANT CELLS AND INDUCES APOPTOSIS

(75) Inventors: Ralph Alexander Willemsen, Rotterdam (NL); Maria Johanna J. E. Van Driel, Rotterdam, legal representative (NL); Johan Renes, Amersfoort (NL)

(73) Assignee: APO-T B.V., Amersfoort (NL)

( * ) Notice: Subject to any disclaimer, the term of this patent is extended or adjusted under 35 U.S.C. 154(b) by 4 days.

This patent is subject to a terminal disclaimer.

(21) Appl. No.: 13/976,974

(22) PCT Filed: Dec. 22, 2011
(Under 37 CFR 1.47)

(86) PCT No.: PCT/NL2011/050891
§ 371 (c)(1),
(2), (4) Date: Nov. 14, 2013

(87) PCT Pub. No.: WO2012/091563
PCT Pub. Date: Jul. 5, 2012

(65) Prior Publication Data
US 2014/0205599 A1    Jul. 24, 2014

(51) Int. Cl.
| C07K 16/00 | (2006.01) |
| A61K 47/48 | (2006.01) |
| C07K 16/28 | (2006.01) |
| C07K 16/30 | (2006.01) |
| A61K 45/06 | (2006.01) |

(52) U.S. Cl.
CPC ........ *A61K 47/48561* (2013.01); *A61K 45/06* (2013.01); *C07K 16/2833* (2013.01); *C07K 16/30* (2013.01); *C07K 2317/21* (2013.01); *C07K 2317/24* (2013.01); *C07K 2317/32* (2013.01); *C07K 2317/34* (2013.01); *C07K 2317/35* (2013.01); *C07K 2317/55* (2013.01); *C07K 2317/56* (2013.01); *C07K 2317/73* (2013.01); *C07K 2319/00* (2013.01)

(58) Field of Classification Search
None
See application file for complete search history.

(56) References Cited

U.S. PATENT DOCUMENTS

| 9,512,231 B2 * | 12/2016 | Willemsen ........ C07K 16/2833 |
| 2009/0268502 A1 | 10/2009 | Miura et al. |
| 2010/0062001 A1 | 3/2010 | Reiter et al. |
| 2010/0158927 A1 | 6/2010 | Reiter et al. |
| 2011/0059076 A1 * | 3/2011 | McDonagh et al. ....... 424/133.1 |

FOREIGN PATENT DOCUMENTS

| WO | 9908108 A1 | 2/1999 |
| WO | 2011/085473 | * 7/2001 |
| WO | 02079222 A2 | 10/2002 |
| WO | 03089467 A1 | 10/2003 |
| WO | 2004050705 A2 | 6/2004 |
| WO | 2005120166 A2 | 12/2005 |
| WO | 2007/073147 | * 6/2007 |
| WO | 2007073147 A1 | 6/2007 |
| WO | 2008120202 A2 | 10/2008 |
| WO | 2012091563 A1 | 7/2012 |
| WO | 2012091564 A2 | 7/2012 |

OTHER PUBLICATIONS

Hickman, Cancer and Metastasis Reviews 11:121 1992.*
Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Willemsen et al., Selection of human antibody fragments directed against tumor T-cell epitopes for adoptive T-cell therapy, Cytometry Part A, vol. 73A, No. 11, (2008).
Willemsen et al., A phage display selected Fab fragment with MHC class I-restricted specificity for MAGE-A1 allows for retargeting of primary human T lymphocytes, Gene Therapy, Nov. 1, 2001, pp. 1601-1608, vol. 8, No. 21.
PCT International Search Report, PCT/NL2011/050891, dated Jun. 12, 2012.

* cited by examiner

*Primary Examiner* — Sheela J Huff
(74) *Attorney, Agent, or Firm* — TraskBritt, P.C.

(57) ABSTRACT

Described are proteinaceous molecules comprising at least a domain that comprises an amino acid sequence that specifically binds to an MHC-peptide complex on an aberrant cell, functionally connected with a substance that induces apoptosis in aberrant cells, but not in normal cells. These proteinaceous molecules are preferably used in selectively modulating biological processes. The provided proteinaceous molecules are of particular use in pharmaceutical compositions for the treatment of diseases related to cellular aberrancies, such as cancers.

6 Claims, 5 Drawing Sheets

SEQUENCE LISTING

<160> NUMBER OF SEQ ID NOS: 52

<210> SEQ ID NO 1
<211> LENGTH: 2226
<212> TYPE: DNA
<213> ORGANISM: Artificial
<220> FEATURE:
<223> OTHER INFORMATION: DNA sequence Hexa-AH5

<400> SEQUENCE: 1

| | | | | | |
|---|---|---|---|---|---|
| cagctgcagc | tgcaagaaag | cggtggtggt | gttgttcagc | ctggtcgtag | cctgcgtctg | 60 |
| agctgtgcag | caagcggttt | tacctttagc | agctatggta | tgcattgggt | tcgtcaggca | 120 |
| ccgggtaagg | aacgtgaagg | tgttgcagtt | attagctatg | atggcagcaa | caaatattat | 180 |
| gccgatagcg | ttaaaggtcg | ctttaccatt | agccgtgata | atagcaaaaa | caccctgtat | 240 |
| ctgcagatga | atagcctgcg | tgcagaagat | accgcagttt | attattgtgc | cggtggtagc | 300 |
| tattatgttc | cggattattg | gggtcagggc | accctggtta | ccgttagcag | cggtagcacc | 360 |
| agcggtagca | tggcccagct | gcaattacaa | gaatcaggtg | gtggcgtggt | gcagccaggt | 420 |
| cgttcactgc | gtctgtcatg | tgcagcatca | ggctttacct | tcagttcata | cggcatgcac | 480 |
| tgggtgcgcc | aagctccagg | caaagaacgc | gaaggcgtgg | ccgttatttc | atacgatggc | 540 |
| tccaataaat | actatgcgga | ttcagtgaaa | ggccgtttta | ccatttcacg | cgataacagt | 600 |
| aaaaacacct | tatacctgca | aatgaattca | ctgcgtgccg | aggatacagc | cgtgtattac | 660 |
| tgtgcgggtg | gttcatatta | cgtgcctgat | tattggggac | aaggtacact | ggtgacagtt | 720 |
| agcagtggta | gtacctcagg | ttcaatggcc | cagttacaac | tgcaagaatc | tggcggtggt | 780 |
| gttgtgcaac | cgggtcgctc | tctgcgtctg | agttgcgctg | catcaggttt | tacattttca | 840 |
| agctacggaa | tgcactgggt | tagacaggct | cccggtaagg | aaagagaagg | cgttgcggtt | 900 |
| atcagttatg | acggtagcaa | taagtattat | gcggactctg | ttaagggtcg | ttttacaatt | 960 |
| tctcgggaca | atagcaagaa | tacactgtac | ttacagatga | actctctgag | agcagaagat | 1020 |
| acagccgtat | actattgcgc | aggcggtagt | tattatgtgc | ctgactactg | gggccaggga | 1080 |
| acgctggtga | ccgtgagtag | cggttcaacc | agcggttcaa | tggcgcaact | gcaacttcaa | 1140 |
| gagtctggtg | gcggtgtggt | acagcctggc | cgttctctgc | gtttaagctg | cgcagcctct | 1200 |
| ggttttacgt | tttcatctta | tggaatgcat | tgggtacgcc | aagcccctgg | aaaagaacgt | 1260 |
| gagggcgtag | cagtgatctc | ttatgatggt | tcgaacaaat | attacgcgga | ctccgtgaaa | 1320 |
| ggacgcttta | caatctctcg | tgataactca | aaaaatacgc | tgtatcttca | aatgaactcc | 1380 |
| ttacgtgcgg | aagatactgc | ggtctattac | tgcgctggcg | gttcttacta | tgtaccagat | 1440 |
| tactggggac | aggggacctt | agttacagtt | agctcaggta | gcaccagtgg | ttctatggct | 1500 |
| caattacagt | tacaagaaag | tggcggtggc | gtggtccaac | ctggccgtag | tctgcgcctg | 1560 |
| tcttgcgcag | cgagcggctt | tacattttct | agttatggca | tgcattgggt | gagacaagct | 1620 |
| ccggggaaag | agcgcgaagg | ggttgcggtg | atttcttatg | acggcagtaa | taaatactac | 1680 |
| gcagatagtg | tgaaaggtcg | tttcacaatt | agtcgcgata | actccaaaaa | cacattatat | 1740 |
| ttgcagatga | acagtttgcg | tgcggaggac | acggctgtat | attattgtgc | aggggttcc | 1800 |
| tactatgtgc | ccgactactg | gggtcaaggg | accttagtga | ccgtttcaag | cggtagtacc | 1860 |
| tctggtagta | tggctcaact | tcagctgcaa | gagtcaggcg | gaggcgttgt | ccagcctgga | 1920 |
| cgctcactgc | gcttaagttg | tgcagccagt | ggctttacgt | ttagctctta | cgggatgcat | 1980 |
| tgggtccggc | aggcgcctgg | gaaggaacgc | gaaggtgtag | ctgtgattag | ttacgatggc | 2040 |

-continued

```
agtaataagt attacgccga ttcagtaaaa ggtcgcttca cgatttcgcg tgataattct  2100
aagaataccc tttaccttca gatgaattcg ttacgcgcag aggataccgc tgtatactac  2160
tgtgctggcg gatcatatta tgtcccagac tattgggggc agggtactct ggtaacggtt  2220
agctct                                                             2226
```

```
<210> SEQ ID NO 2
<211> LENGTH: 123
<212> TYPE: PRT
<213> ORGANISM: Artificial
<220> FEATURE:
<223> OTHER INFORMATION: Amino acid sequence AH5

<400> SEQUENCE: 2

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Arg Glu Gly Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ser Tyr Tyr Val Pro Asp Tyr Trp Gly Gln Gly Thr Leu
            100                 105                 110

Val Thr Val Ser Ser Gly Ser Thr Ser Gly Ser
        115                 120
```

```
<210> SEQ ID NO 3
<211> LENGTH: 121
<212> TYPE: PRT
<213> ORGANISM: Artificial
<220> FEATURE:
<223> OTHER INFORMATION: Amino acid sequence apoptin

<400> SEQUENCE: 3

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Lys Arg Arg Ile Arg Leu
        115                 120
```

```
<210> SEQ ID NO 4
```

```
<211> LENGTH: 5
<212> TYPE: PRT
<213> ORGANISM: Artificial
<220> FEATURE:
<223> OTHER INFORMATION: Linker peptide
<220> FEATURE:
<221> NAME/KEY: MISC_FEATURE
<222> LOCATION: (1)..(5)
<223> OTHER INFORMATION: this sequence may be repeated n times, where n
      is a positive integer

<400> SEQUENCE: 4

Gly Gly Gly Gly Ser
1               5

<210> SEQ ID NO 5
<211> LENGTH: 6
<212> TYPE: PRT
<213> ORGANISM: Artificial
<220> FEATURE:
<223> OTHER INFORMATION: Linker peptide
<220> FEATURE:
<221> NAME/KEY: MISC_FEATURE
<222> LOCATION: (1)..(6)
<223> OTHER INFORMATION: this sequence may be repeated n times, where n
      is a positive integer

<400> SEQUENCE: 5

Gly Ser Thr Ser Gly Ser
1               5

<210> SEQ ID NO 6
<211> LENGTH: 18
<212> TYPE: PRT
<213> ORGANISM: Artificial
<220> FEATURE:
<223> OTHER INFORMATION: Linker peptide

<400> SEQUENCE: 6

Gly Ser Thr Ser Gly Ser Gly Lys Pro Gly Ser Gly Glu Gly Ser Thr
1               5                   10                  15

Lys Gly

<210> SEQ ID NO 7
<211> LENGTH: 23
<212> TYPE: PRT
<213> ORGANISM: Artificial
<220> FEATURE:
<223> OTHER INFORMATION: Linker peptide

<400> SEQUENCE: 7

Glu Phe Ala Lys Thr Thr Ala Pro Ser Val Tyr Pro Leu Ala Pro Val
1               5                   10                  15

Leu Glu Ser Ser Gly Ser Gly
            20

<210> SEQ ID NO 8
<211> LENGTH: 10
<212> TYPE: PRT
<213> ORGANISM: Artificial
<220> FEATURE:
<223> OTHER INFORMATION: IgG1 Linker peptide

<400> SEQUENCE: 8

Glu Pro Lys Ser Cys Asp Lys Thr His Thr
1               5                   10
```

```
<210> SEQ ID NO 9
<211> LENGTH: 12
<212> TYPE: PRT
<213> ORGANISM: Artificial
<220> FEATURE:
<223> OTHER INFORMATION: IgG3 Linker peptide

<400> SEQUENCE: 9

Glu Leu Lys Thr Pro Leu Gly Asp Thr Thr His Thr
1               5                   10

<210> SEQ ID NO 10
<211> LENGTH: 7
<212> TYPE: PRT
<213> ORGANISM: Artificial
<220> FEATURE:
<223> OTHER INFORMATION: IgG4 Linker peptide

<400> SEQUENCE: 10

Glu Ser Lys Tyr Gly Pro Pro
1               5

<210> SEQ ID NO 11
<211> LENGTH: 9
<212> TYPE: PRT
<213> ORGANISM: Artificial
<220> FEATURE:
<223> OTHER INFORMATION: Amino acid sequence MHC-1 HLA-A0201 presentable
      peptide in MAGE-A

<400> SEQUENCE: 11

Tyr Leu Glu Tyr Arg Gln Val Pro Gly
1               5

<210> SEQ ID NO 12
<211> LENGTH: 9
<212> TYPE: PRT
<213> ORGANISM: Artificial
<220> FEATURE:
<223> OTHER INFORMATION: Amino acid sequence MCH-1 HLA-CW7 presentable
      peptide in MAGE-A

<400> SEQUENCE: 12

Glu Gly Asp Cys Ala Pro Glu Glu Lys
1               5

<210> SEQ ID NO 13
<211> LENGTH: 121
<212> TYPE: PRT
<213> ORGANISM: Artificial
<220> FEATURE:
<223> OTHER INFORMATION: Amino acid sequence Vh binding domain 11H

<400> SEQUENCE: 13

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Leu
        35                  40                  45

Ser Tyr Ile Ser Ser Asp Gly Ser Thr Ile Tyr Tyr Ala Asp Ser Val
    50                  55                  60

Lys Gly Arg Phe Thr Val Ser Arg Asp Asn Ala Lys Asn Ser Leu Ser
65                  70                  75                  80

Leu Gln Met Asn Ser Leu Arg Ala Asp Asp Thr Ala Val Tyr Tyr Cys
```

```
                    85                  90                  95
Ala Val Ser Pro Arg Gly Tyr Tyr Tyr Gly Leu Asp Leu Trp Gly
                100                 105                 110
Gln Gly Thr Thr Val Thr Val Ser Ser
            115                 120

<210> SEQ ID NO 14
<211> LENGTH: 119
<212> TYPE: PRT
<213> ORGANISM: Artificial
<220> FEATURE:
<223> OTHER INFORMATION: Amino acid sequence AH5 Vh binding domain

<400> SEQUENCE: 14

Met Ala Gln Leu Gln Leu Gln Glu Ser Gly Gly Gly Val Val Gln Pro
1               5                   10                  15

Gly Arg Ser Leu Arg Leu Ser Cys Ala Ala Ser Gly Phe Thr Phe Ser
                20                  25                  30

Ser Tyr Gly Met His Trp Val Arg Gln Ala Pro Gly Lys Glu Arg Glu
            35                  40                  45

Gly Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gly Gly Ser Tyr Tyr Val Pro Asp Tyr Trp Gly Gln Gly
                100                 105                 110

Thr Leu Val Thr Val Ser Ser
            115

<210> SEQ ID NO 15
<211> LENGTH: 117
<212> TYPE: PRT
<213> ORGANISM: Artificial
<220> FEATURE:
<223> OTHER INFORMATION: Amino acid sequence AH5 Vh binding domain

<400> SEQUENCE: 15

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Glu Arg Glu Gly Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ser Tyr Tyr Val Pro Asp Tyr Trp Gly Gln Gly Thr Leu
                100                 105                 110

Val Thr Val Ser Ser
            115

<210> SEQ ID NO 16
<211> LENGTH: 10
```

```
<212> TYPE: PRT
<213> ORGANISM: Artificial
<220> FEATURE:
<223> OTHER INFORMATION: Linker peptide

<400> SEQUENCE: 16

Gly Gly Gly Gly Ser Gly Gly Gly Gly Ser
1               5                   10

<210> SEQ ID NO 17
<211> LENGTH: 120
<212> TYPE: PRT
<213> ORGANISM: Artificial
<220> FEATURE:
<223> OTHER INFORMATION: Amino acid sequence AH5 Vh binding domain

<400> SEQUENCE: 17

Asn Ala Leu Gln Glu Asp Thr Pro Pro Gly Pro Ser Thr Val Phe Arg
1               5                   10                  15

Pro Pro Thr Ser Ser Arg Pro Leu Glu Thr Pro His Cys Arg Glu Ile
            20                  25                  30

Arg Ile Gly Ile Ala Gly Ile Thr Ile Thr Leu Ser Leu Cys Gly Cys
        35                  40                  45

Ala Asn Ala Arg Ala Pro Thr Leu Arg Ser Ala Thr Ala Asp Asn Ser
    50                  55                  60

Glu Ser Thr Gly Phe Lys Asn Val Pro Asp Leu Arg Thr Asp Gln Pro
65                  70                  75                  80

Lys Pro Pro Ser Lys Lys Arg Ser Cys Asp Pro Ser Glu Tyr Arg Val
                85                  90                  95

Ser Glu Leu Lys Glu Ser Leu Ile Thr Thr Pro Ser Arg Pro Arg
            100                 105                 110

Thr Ala Lys Arg Arg Ile Arg Leu
            115                 120

<210> SEQ ID NO 18
<211> LENGTH: 17
<212> TYPE: PRT
<213> ORGANISM: Artificial
<220> FEATURE:
<223> OTHER INFORMATION: Amino acid sequence cathepsin L cleavage site

<400> SEQUENCE: 18

Arg Lys Glu Leu Val Thr Pro Ala Arg Asp Phe Gly His Phe Gly Leu
1               5                   10                  15

Ser

<210> SEQ ID NO 19
<211> LENGTH: 137
<212> TYPE: PRT
<213> ORGANISM: Artificial
<220> FEATURE:
<223> OTHER INFORMATION: Amino acid sequence AH5 Vh binding domain

<400> SEQUENCE: 19

Arg Lys Glu Leu Val Thr Pro Ala Arg Asp Phe Gly His Phe Gly Leu
1               5                   10                  15

Ser Asn Ala Leu Gln Glu Asp Thr Pro Pro Gly Pro Ser Thr Val Phe
            20                  25                  30

Arg Pro Pro Thr Ser Ser Arg Pro Leu Glu Thr Pro His Cys Arg Glu
        35                  40                  45

Ile Arg Ile Gly Ile Ala Gly Ile Thr Ile Thr Leu Ser Leu Cys Gly
```

```
                    50                  55                  60
Cys Ala Asn Ala Arg Ala Pro Thr Leu Arg Ser Ala Thr Ala Asp Asn
 65                  70                  75                  80

Ser Glu Ser Thr Gly Phe Lys Asn Val Pro Asp Leu Arg Thr Asp Gln
                 85                  90                  95

Pro Lys Pro Pro Ser Lys Lys Arg Ser Cys Asp Pro Ser Glu Tyr Arg
            100                 105                 110

Val Ser Glu Leu Lys Glu Ser Leu Ile Thr Thr Thr Pro Ser Arg Pro
        115                 120                 125

Arg Thr Ala Lys Arg Arg Ile Arg Leu
    130                 135
```

<210> SEQ ID NO 20
<211> LENGTH: 10
<212> TYPE: PRT
<213> ORGANISM: Artificial
<220> FEATURE:
<223> OTHER INFORMATION: Amino acid sequence cathepsin -B cleavage site

<400> SEQUENCE: 20

```
Gly Phe Gln Gly Val Gln Phe Ala Gly Phe
1               5                   10
```

<210> SEQ ID NO 21
<211> LENGTH: 9
<212> TYPE: PRT
<213> ORGANISM: Artificial
<220> FEATURE:
<223> OTHER INFORMATION: Amino acid sequence of MAGE-A3 peptide epitope
      binding to HLA

<400> SEQUENCE: 21

```
Ile Met Pro Lys Ala Gly Leu Leu Ile
1               5
```

<210> SEQ ID NO 22
<211> LENGTH: 9
<212> TYPE: PRT
<213> ORGANISM: Artificial
<220> FEATURE:
<223> OTHER INFORMATION: Amino acid sequence MHC-1 HLA-A0201 presentable
      peptide in MAGE-A1

<400> SEQUENCE: 22

```
Tyr Leu Glu Tyr Arg Gln Val Pro Asp
1               5
```

<210> SEQ ID NO 23
<211> LENGTH: 9
<212> TYPE: PRT
<213> ORGANISM: Artificial
<220> FEATURE:
<223> OTHER INFORMATION: Amino acid sequence MHC-1 HLA-A0201 presentable
      peptide in MAGE-A1, with enhanced binding capacity for HLA-A0201

<400> SEQUENCE: 23

```
Tyr Leu Glu Tyr Arg Gln Val Pro Val
1               5
```

<210> SEQ ID NO 24
<211> LENGTH: 16
<212> TYPE: PRT
<213> ORGANISM: Artificial
<220> FEATURE:
<223> OTHER INFORMATION: Amino acid sequence of MAGE-A3 peptide epitope -continued binding to HLA

<400> SEQUENCE: 24

Lys Lys Leu Leu Thr Gln His Phe Val Gln Glu Asn Tyr Leu Glu Tyr
1               5                   10                  15

<210> SEQ ID NO 25
<211> LENGTH: 9
<212> TYPE: PRT
<213> ORGANISM: Artificial
<220> FEATURE:
<223> OTHER INFORMATION: Amino acid sequence of MAGE peptide epitope
      binding to HLA

<400> SEQUENCE: 25

Glu Ala Asp Pro Thr Gly His Ser Tyr
1               5

<210> SEQ ID NO 26
<211> LENGTH: 9
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 26

Ser Leu Phe Arg Ala Val Ile Thr Lys
1               5

<210> SEQ ID NO 27
<211> LENGTH: 9
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 27

Asn Tyr Lys His Cys Phe Pro Glu Ile
1               5

<210> SEQ ID NO 28
<211> LENGTH: 10
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 28

Glu Val Tyr Asp Gly Arg Glu His Ser Ala
1               5                   10

<210> SEQ ID NO 29
<211> LENGTH: 10
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 29

Arg Glu Pro Val Thr Lys Ala Glu Met Leu
1               5                   10

<210> SEQ ID NO 30

```
<211> LENGTH: 9
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 30

Asp Pro Ala Arg Tyr Glu Phe Leu Trp
1               5

<210> SEQ ID NO 31
<211> LENGTH: 9
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 31

Ser Ala Phe Pro Thr Thr Ile Asn Phe
1               5

<210> SEQ ID NO 32
<211> LENGTH: 9
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 32

Ser Ala Tyr Gly Glu Pro Arg Lys Leu
1               5

<210> SEQ ID NO 33
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 33

Lys Met Val Glu Leu Val His Phe Leu
1               5

<210> SEQ ID NO 34
<211> LENGTH: 10
<212> TYPE: PRT
<213> ORGANISM: Artificial
<220> FEATURE:
<223> OTHER INFORMATION: amino acid sequence of MAGE peptide binding to
      HLA

<400> SEQUENCE: 34

Tyr Leu Gln Leu Val Phe Gly Ile Glu Val
1               5                   10

<210> SEQ ID NO 35
<211> LENGTH: 9
<212> TYPE: PRT
<213> ORGANISM: Artificial
<220> FEATURE:
<223> OTHER INFORMATION: amino acid sequence of MAGE peptide epitope
      binding to HLA

<400> SEQUENCE: 35
```

```
Glu Tyr Leu Gln Leu Val Phe Gly Ile
1               5
```

<210> SEQ ID NO 36
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 36

```
Glu Ala Asp Pro Ile Gly His Leu Tyr
1               5
```

<210> SEQ ID NO 37
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 37

```
Phe Leu Trp Gly Pro Arg Ala Leu Val
1               5
```

<210> SEQ ID NO 38
<211> LENGTH: 10
<212> TYPE: PRT
<213> ORGANISM: Artificial
<220> FEATURE:
<223> OTHER INFORMATION: amino acid sequence of MAGE peptide binding to
      HLA

<400> SEQUENCE: 38

```
Met Glu Val Asp Pro Ile Gly His Leu Tyr
1               5                   10
```

<210> SEQ ID NO 39
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 39

```
Trp Gln Tyr Phe Phe Pro Val Ile Phe
1               5
```

<210> SEQ ID NO 40
<211> LENGTH: 10
<212> TYPE: PRT
<213> ORGANISM: Artificial
<220> FEATURE:
<223> OTHER INFORMATION: amino acid sequence of MAGE peptide binding to
      HLA

<400> SEQUENCE: 40

```
Gly Val Tyr Asp Gly Arg Glu His Thr Val
1               5                   10
```

<210> SEQ ID NO 41
<211> LENGTH: 9
<212> TYPE: PRT
<213> ORGANISM: Artificial
<220> FEATURE:

```
<223> OTHER INFORMATION: amino acid sequence of MAGE peptide binding to
      HLA

<400> SEQUENCE: 41

Met Val Lys Ile Ser Gly Gly Pro Arg
1               5

<210> SEQ ID NO 42
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 42

Gly Leu Tyr Asp Gly Met Glu His Leu
1               5

<210> SEQ ID NO 43
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 43

Val Arg Ile Gly His Leu Tyr Ile Leu
1               5

<210> SEQ ID NO 44
<211> LENGTH: 9
<212> TYPE: PRT
<213> ORGANISM: Artificial
<220> FEATURE:
<223> OTHER INFORMATION: amino acid sequence of MAGE peptide binding to
      HLA

<400> SEQUENCE: 44

Ala Ala Arg Ala Val Phe Leu Ala Leu
1               5

<210> SEQ ID NO 45
<211> LENGTH: 9
<212> TYPE: PRT
<213> ORGANISM: Artificial
<220> FEATURE:
<223> OTHER INFORMATION: amino acid sequence of DAM-6 and DAM-10 peptide
      epitope binding to HLA

<400> SEQUENCE: 45

Phe Leu Trp Gly Pro Arg Ala Tyr Ala
1               5

<210> SEQ ID NO 46
<211> LENGTH: 8
<212> TYPE: PRT
<213> ORGANISM: Artificial
<220> FEATURE:
<223> OTHER INFORMATION: amino acid sequence of GAGE-1/-2/-8 peptide
      epitope binding to HLA

<400> SEQUENCE: 46

Tyr Arg Pro Arg Pro Arg Arg Tyr
1               5
```

```
<210> SEQ ID NO 47
<211> LENGTH: 9
<212> TYPE: PRT
<213> ORGANISM: Artificial
<220> FEATURE:
<223> OTHER INFORMATION: amino acid sequence of GAGE-3/-4/-5/-6/-7B
      peptide epitope binding to HLA

<400> SEQUENCE: 47

Tyr Tyr Trp Pro Arg Pro Arg Arg Tyr
1               5

<210> SEQ ID NO 48
<211> LENGTH: 11
<212> TYPE: PRT
<213> ORGANISM: Artificial
<220> FEATURE:
<223> OTHER INFORMATION: amino acid sequence of NA88-A peptide epitope
      binding to HLA

<400> SEQUENCE: 48

Met Thr Gln Gly Gln His Phe Leu Gln Lys Val
1               5                   10

<210> SEQ ID NO 49
<211> LENGTH: 11
<212> TYPE: PRT
<213> ORGANISM: Artificial
<220> FEATURE:
<223> OTHER INFORMATION: amino acid sequence of NY-ESO-1 peptide epitope
      binding to HLA

<400> SEQUENCE: 49

Ser Leu Leu Met Trp Ile Thr Gln Cys Phe Leu
1               5                   10

<210> SEQ ID NO 50
<211> LENGTH: 9
<212> TYPE: PRT
<213> ORGANISM: Artificial
<220> FEATURE:
<223> OTHER INFORMATION: amino acid sequence of NY-ESO-1a peptide
      epitope binding to HLA

<400> SEQUENCE: 50

Ser Leu Leu Met Trp Ile Thr Gln Cys
1               5

<210> SEQ ID NO 51
<211> LENGTH: 9
<212> TYPE: PRT
<213> ORGANISM: Artificial
<220> FEATURE:
<223> OTHER INFORMATION: amino acid sequence of NY-ESO-1a peptide
      epitope binding to HLA

<400> SEQUENCE: 51

Gln Leu Ser Leu Leu Met Trp Ile Thr
1               5

<210> SEQ ID NO 52
<211> LENGTH: 10
<212> TYPE: PRT
<213> ORGANISM: Artificial
<220> FEATURE:
<223> OTHER INFORMATION: amino acid sequence of NY-ESO-1a peptide
      epitope binding to HLA
```

-continued

```
<400> SEQUENCE: 52

Ala Ser Gly Pro Gly Gly Gly Ala Pro Arg
1               5                   10
```

US 9,821,073 B2

POLYPEPTIDE THAT BINDS ABERRANT CELLS AND INDUCES APOPTOSIS

CROSS-REFERENCE TO RELATED APPLICATIONS

This application is a national phase entry under 35 U.S.C. §371 of International Patent Application PCT/NL2011/050891, filed Dec. 22, 2011, designating the United States of America and published in English as International Patent Publication WO 2012/091563 A1 on Jul. 5, 2012, which claims the benefit under Article 8 of the Patent Cooperation Treaty and under 35 U.S.C. §119(e) to U.S. Provisional Patent Application Ser. No. 61/460,212, filed Dec. 27, 2010.

TECHNICAL FIELD

The disclosure relates to the field of biotherapeutics. It also relates to the field of tumor biology. More in particular, it relates to specific binding molecules that induce cell death, in particular, programmed cell death (apoptosis) in aberrant cells such as tumor cells. More specifically, one or multiple antibody variable fragments connected with a cell death-inducing agent such as apoptin are provided that specifically target MHC-peptide complexes on aberrant cells, thereby delivering a cell death-inducing agent such as apoptin that induces apoptosis upon uptake of the specific binding molecule. It also relates to the use of these apoptosis-inducing binding molecules in selectively killing cancer cells and other aberrant cells.

BACKGROUND

Since the sixties of the last century, it has been proposed to use the specific binding power of the immune system (T cells and antibodies) to selectively kill tumor cells but leave alone the normal cells in a patient's body. Many tumor antigens that could be targeted by, in particular, antibodies, like carcino-embryonic antigen (CEA), alpha-fetoprotein (AFP) and so on, have been suggested since those days, but for essentially all of these antigens, expression is associated with normal tissue as well. Thus, so far, selective killing of aberrant cells has been an elusive goal.

The primary immunological function of MHC molecules is to bind and to "present" antigenic peptides to form an MHC-peptide (MHC-p) complex on the surface of cells for recognition and binding by antigen-specific T-cell receptors (TCRs) of lymphocytes. Antigenic peptides are also referred to as epitopes, both of which have basically the same meaning throughout the application. Two classes of MHC-p complexes can be distinguished with regard to their function:

(i) MHC class I-p complexes can be expressed by almost all nucleated cells in order to attract $CD8^+$ cytotoxic T cells, and (ii) MHC class II-p complexes are constitutively expressed only on so-called antigen-presenting cells (APCs), such as B lymphocytes, macrophages or dendritic cells (DCs).

MHC class I-p complexes are composed of a variable heavy chain, an invariable β-microglobulin and an antigenic peptide. The MHC class II molecules are characterized by distinctive α and β polypeptide subunits that combine to form αβ heterodimers characteristic of mature MHC class II molecules. Differential structural properties of MHC class I and class II molecules account for their respective roles in activating different populations of T lymphocytes. Cytotoxic $T_C$ lymphocytes (CTLs) bind antigenic peptides presented by MHC class I molecules. Helper $T_H$ lymphocytes bind antigenic peptides presented by MHC class II molecules. MHC class I and class II molecules differentially bind CD8 and CD4 cell adhesion molecules. MHC class I molecules are specifically bound by CD8 molecules expressed on CTLs, whereas MHC class II molecules are specifically bound by CD4 molecules expressed on helper $T_H$ lymphocytes.

The sizes of the antigenic peptide-binding pockets of MHC class I and class II molecules differ; class I molecules bind smaller antigenic peptides, typically eight to ten amino acid residues in length, whereas class II molecules bind larger antigenic peptides, typically 13 to 18 amino acid residues in length.

In humans, MHC molecules are termed human leukocyte antigens (HLA). HLA-associated peptides are short, encompassing typically 9 to 25 amino acid residues. Humans synthesize three different types of class I molecules designated HLA-A, HLA-B, and HLA-C. Human class II molecules are designated HLA-D, e.g., HLA-DR.

The MHC expressed on all nucleated cells of humans and of animals plays a crucial role in immunological defense against pathogens and cancer. The transformation of normal cells to aberrant cancer cells involves several major changes in gene expression. This results in profound changes in the antigenic composition of cells. It is well established that new antigenic entities are presented as MHC-restricted tumor antigens. As such, the MHC class I and MHC class II systems may be seen as nature's proteomic scanning chips, continuously processing intracellular proteins, generating antigenic peptides for presentation on the cell surface. If these antigenic peptides elicit an immune reactivity, the transformed cells are killed by the cellular immune system. However, if the transformed cells resist immune-mediated cell killing, cancer may develop.

Antibodies that bind MHC class I molecules on various cell types have been studied in detail for their mode of action. Mouse monoclonal antibodies that bind the MHC class I α1 domain of the MHC class I α chain induce apoptosis in activated T cells, but not in resting T cells. Other reports mention antibodies specific for, e.g., the α3 domain of MHC class I, which induce growth inhibition and apoptosis in B-cell-derived cancer cells. However, in this case, a secondary cross-linking antibody was required for the induction of apoptosis (A. E. Pedersen et al., *Exp. Cell Res.* 1999, 251:128-34).

Antibodies binding to β2-microglobulin (β2-M), an essential component of the MHC class I molecules, also induce apoptosis. Several hematologic cancer cells treated with anti-β2M antibodies were killed efficiently, both in vitro and in vivo (Y. Cao et al., *Br. J. Haematol.* 2011, 154:111-121).

Thus, it is known that binding of MHC class I or MHC class II molecules by several anti-MHC antibodies can have an apoptosis-inducing effect. However, the therapeutic application of these anti-MHC antibodies has been hampered by the lack of target cell specificity. Since these antibodies are directed primarily against a constant domain of the MHC molecule, the cell surface expression of the MHC constant domain determines whether or not a cell can be triggered by the antibody to undergo apoptosis. Because MHC class I and MHC class II molecules are expressed on both normal and aberrant cells, it is clear that these antibodies cannot discriminate between normal and aberrant cells. As a consequence, their therapeutic value is significantly reduced, if not abolished by the side effects caused by unwanted apoptosis of healthy cells. According to the invention, antibodies that specifically recognize MHC-presented antigenic peptides derived from cancer antigens would, therefore, dramatically expand the therapeutic repertoire, if they could be shown to have anti-cancer cell activity. In addition, current methods to induce apoptosis via MHC class I or MHC class II may depend on external cross-linking of anti-MHC antibodies.

Obtaining antibodies binding to MHC-p complexes and not binding to MHC molecules not loaded with the antigenic peptide remains a laborious task and several failures have been reported. The first available antibodies have been obtained after immunization of mice with recombinant MHC-p complexes or peptide-loaded TAP-deficient antigen-presenting cells. More recently, antibodies have been obtained by selection from phage-antibody libraries made from immunized transgenic mice or by selection from completely human antibody phage libraries. Immunization with MHC-p complexes is extremely time consuming. Moreover, antibodies of murine origin cannot be used repetitively in patients because of the likely development of a human anti-mouse antibody response (so-called anti-drug antibodies, ADA). Antibodies derived from phage display, in general, display low affinity for the antigen and thus may require additional modifications before they can be used efficiently. According to the invention, the antibody specificities are preferably selected through phage (or yeast) display, whereby an MHC molecule loaded with a cancer-related peptide is presented to the library. Details are given in the experimental part. The antibody specificities according to the invention are checked for specificity to the MHC-peptide complex and should not recognize (to any significant extent) MHC loaded with irrelevant peptides or the peptides by themselves.

Cancer is caused by oncogenic transformation in aberrant cells, which drives uncontrolled cell proliferation, leading to misalignment of cell-cycle checkpoints, DNA damage and metabolic stress. These aberrations should direct tumor cells toward an apoptotic path that has evolved in multi-cellular animals as a means of eliminating abnormal cells that pose a threat to the organism. Indeed, most transformed cells or tumorigenic cells are killed by apoptosis. However, occasionally, a cell with additional mutations that enable avoidance of apoptotic death survives, thus enabling its malignant progression. Thus, cancer cells can grow, not only due to imbalances in proliferation and/or cell cycle regulation, but also due to imbalances in their apoptosis machinery. Imbalances like, for example, genomic mutations resulting in non-functional apoptosis-inducing proteins or over-expression of apoptosis-inhibiting proteins, form the basis of tumor formation. Fortunately, even cells that manage to escape the apoptosis signals this way when activated by their aberrant phenotype, are still primed for eradication from the organism. Apoptosis in these aberrant cells can still be triggered upon silencing or overcoming the apoptosis-inhibiting signals induced by mutations. Traditional cancer therapies can activate apoptosis, but they do so indirectly and often encounter tumor resistance. Direct and selective targeting of key components of the apoptosis machinery in these aberrant cells is a promising strategy for development of new anti-tumor therapeutics. Selective activation of the apoptosis pathway would allow for halting tumor growth and would allow for induction of tumor regression.

A disadvantage of many, if not all, anti-tumor drugs currently on the market or in development, which are based on targeting the apoptosis machinery, is that these drugs do not discriminate between aberrant cells and healthy cells. This non-specificity bears a challenging risk for drug-induced adverse events. Examples of such unwanted side effects are well known to the field: radiotherapy and chemotherapeutics induce apoptosis only as a secondary effect of the damage they cause to vital cellular components. Not only aberrant cells are targeted, though, in fact, most proliferating cells including healthy cells respond to the apoptosis-stimulating therapy. Therefore, a disadvantage of current apoptosis-inducing compounds is their non-selective nature, which reduces their potential.

In an earlier application (WO2007/073147; Apoptosis-inducing protein complexes and therapeutic use thereof, incorporated herein by reference), it is disclosed that a polypeptide complex achieves the goal of (specifically) killing, e.g., tumor cells by specifically targeting these cells and, as a result, induces apoptosis in these tumor cells. Although it is undesirable to be bound by theory, at present, it is believed that this is the result of cross-linking of cell-surface-expressed protein-protein complexes by multiple interactions with the multivalent polypeptide complex of that invention.

Two interlinked signaling pathways control apoptosis activation. Intracellular signals, such as DNA damage, drive apoptosis primarily through the intrinsic pathway, controlled by the Bcl-2 protein family. Extracellular signals, usually generated by cytotoxic cells of the immune system such as natural killer cells or cytotoxic T cells, trigger apoptosis mainly through the extrinsic pathway. Both pathways stimulate caspases with apoptosis-inducing activity. Caspases are a family of cysteine proteases, which are present in most cells as pro-caspases and which are activated through the so-called caspase cascade. Apoptotic signals first stimulate upstream initiator caspases (amongst others, caspases 8, 9 and 10) by recruiting them into specific signaling complexes that promote their multimerization. In turn, these caspases in signaling complexes activate downstream effector caspases (including caspases 3, 6 and 7) by proteolytic processing. These effector caspases then, in turn, process various cellular proteins, resulting in the apoptotic cell death program.

Some viruses (or at least some of their proteins), such as chicken anemia virus (CAV), parvovirus minute virus of mice (MVM), engineered herpes simplex virus, reovirus, vesicular stomatitis virus, adenovirus type 2 and poxvirus such as vaccinia, can selectively and preferentially kill tumor cells. These viruses do so through activation of the apoptosis machinery of the aberrant cell infected by the virus. The viruses are able to specifically provide the effective apoptosis-inducing death signal, which can interact with one or more of the derailed cancer processes. Fortunately, these viruses (or their proteins) have the ability to efficiently target cell death program in aberrant cells, although this cell death program might be derailed as a consequence of its aberrant nature. Two oncolytic virus-based therapies are tested in clinical trials: Reolysin, which is a reovirus, and Onyx-015, which is an adenovirus deletion mutant. The various clinical trials revealed that the therapeutic agents were selective for cancer cells, but therapeutic potency was limited. In general, anti-tumor gene therapy has largely failed to date in patients owing to inefficient delivery of the gene to sufficient numbers of cancer cells locally and systemically. Development of new generation anti-tumor drugs should, therefore, focus on improved anticancer potency, improved efficacy of delivery and improved systemic spread.

Interestingly, proteins derived from several of these viruses, i.e., CAV-derived apoptosis-inducing apoptin, adenovirus early region 4 open reading frame (E4orf4) and parvovirus-H1-derived non-structural protein 1 (NS1), were identified as agents that are able to induce aberrant-cell apoptosis. For example, apoptin was shown to be the main aberrant cell-specific apoptosis-inducing factor of CAV. In addition to these apoptosis-inducing proteins identified in these viruses, new apoptosis-inducing proteins were identified that are not part of viruses' genomes but that are also able to induce cell death specifically in aberrant cells. Examples are human α-lactalbumin made lethal to tumor cells (HAMLET), human cytokines melanoma differentiation-associated gene-7 (mda-7) and tumor necrosis factor-related apoptosis-inducing ligand (TRAIL).

The ability of these viral proteins apoptin, E4orf4 and NS1 and these non-viral cellular proteins HAMLET, TRAIL and mda-7 to induce apoptosis in aberrant cells renders them with a high potency for beneficial incorporation in anti-tumor therapies.

Parvovirus-H1 NS1 protein induces cell death in glioma cells. The tumor-selective apoptosis-inducing activity of NS1 is related to its interaction with the catalytic subunit of casein kinase II (CKIIα). Formation of NS1-CKIIα complexes points to interference by NS1 with intracellular signaling processes (Noteborn, *Eur. J. Pharm.*, 2009). As a result of the formed NS1-CKIIα complexes, CKIIα-dependent cytoskeletal changes occur followed by apoptosis. Parvovirus-H1 infections induce characteristic changes within the cytoskeleton filaments of tumor cells, which results finally in the degradation of actin fibers and the appearance of so-called actin patches.

Loss of p53 functioning is related to tumor formation and is at the basis of resistance of tumors to various anticancer therapies. The adenovirus-derived protein E4orf4 selectively kills tumor cells independent of p53 (Noteborn, *Eur. J. Pharm.*, 2009). Like parvovirus-H1-derived protein NS1, E4orf4 expression results in deregulation of the cytoskeleton. E4orf4-induced cell death is not dependent on classical caspase pathways, and E4orf4 circumvents Bcl-2 blockage of apoptosis and does not require release of mitochondrial cytochrome c. Seemingly, E4orf4 is able to trigger apoptosis in aberrant cells via an alternative cell death process not present in non-aberrant cells.

Human α-lactalbumin made lethal to tumor cells (HAMLET) is a structural derivative of α-lactalbumin, a main protein of human milk. HAMLET can induce apoptosis in a tumor-selective manner (Noteborn, *Eur. J. Pharm.*, 2009). The precursor of HAMLET is α-lactalbumin, which undergoes structural changes upon binding of oleic acid and subsequent release of calcium ions. HAMLET can specifically kill aberrant cells of skin papillomas, glioblastoma tumors, and bladder cancers by efficient uptake, leaving healthy tissue unaltered. HAMLET acts on the caspase pathways due to stimulated release of cytochrome c from the mitochondria. In the nuclei of tumor cells, HAMLET associates with histones resulting in an irreversible disruption of the chromatin organization. This seems the key event responsible for the tumor-cell killing activity of HAMLET, apart from its ability to activate 20S proteasomes. HAMLET induces tumor-selective apoptosis in a p53-independent manner.

Melanoma differentiation-associated gene-7 (mda-7; interleukin 24), an interleukin-10 family member, induces apoptosis in various cancer cells dependent on caspases (Noteborn, *Eur. J. Pharm.*, 2009). For example, apoptosis-inducing activity of mda-7 upon down-regulation of survival signals such as Bcl-2 and Akt by mda-7 is seen in breast cancer cells when adenoviral-induced mda-7 is used. Also secreted mda-7 exposes anti-tumor cell activity on distant tumor cells. Specificity of mda-7 apoptosis-inducing activity is based on the activation of the FasL/TRAIL pathways. Mda-7 has been proven effective pre-clinically in treatment of subcutaneous ovarian cancer xenografts and lung tumor xenografts (combination therapy), when adenovirus-expressing mda-7 was used. A clinical phase I trial revealed that subsets of tumor cells are resistant to mda-7, leaving substantial room for further improvement of therapies based on proteins bearing apoptosis-inducing activity.

The tumor necrosis factor-related apoptosis-inducing ligand (TRAIL) induces both p53-dependent and p53-independent apoptosis in tumor cells (Noteborn, *Eur. J. Pharm.*, 2009). TRAIL activates the extrinsic apoptosis pathway leading to caspase 8 and subsequently amongst other caspase-3 activation. Subsequently, TRAIL-induced apoptosis activates the intrinsic apoptosis pathway. One of the first steps in TRAIL-induced apoptosis is the binding of TRAIL to death receptors DR4 and DR5. TRAIL's apoptosis activity is selective for tumor cells but the diversity of tumor cells susceptible to TRAIL-induced apoptosis is limited. This is perhaps due to the fact that TRAIL signaling also activates NF-κB, which induces anti-apoptotic regulators. In addition or alternatively, TRAIL resistance of several types of tumor cells may be due to the fact that these tumor cells over-express anti-apoptosis protein FLIP or Bcl-2.

The CAV-derived apoptin is a viral protein with apoptosis-inducing activity toward a broad range of human aberrant cell types but not toward normal, non-transformed human diploid cells including primary human hepatocytes and stem cells. A broad variety of tumor cell types is susceptible to apoptin's apoptosis-inducing activity. This apoptin activity can be triggered by induced transformation of cells. These two observations point to regulation of the apoptosis pathway by apoptin during an early stage of the cell transformation process. The specificity of apoptin for tumor cells may be related to its multimeric nature when in its active form, its interaction with chromatin structures in tumor cells, its selective phosphorylation in malignant cells, and its ability to elevate ceramide levels in tumor cells, which is a tumor suppressor activity. This latter activity is indicative for an important role of sphingolipids in apoptin-induced apoptosis. Apoptin induces apoptosis also by acting on and interfering with the cell cycle processes. That is to say, apoptin acts mainly via interaction with the anaphase-promoting complex/cyclosome complex, inducing G2/M cell cycle arrest resulting in p73/PUMA-mediated apoptosis. Cytochrome c release and activation of the central caspase pathways are involved in apoptin-induced cell death. The selectivity of apoptin's apoptosis-inducing activity for tumor cells is p53 independent and, in several tumor cell types, is not sensitive to Bcl-xl and even stimulated by Bcl-2. In noimal cells, apoptin is found located mainly in the cytoplasm. In transformed cells and in malignant cells characterized by metaplasia, hyperplasia or dysplasia, apoptin localizes (also) in the nucleus (Danen-van Oorschot et al., 1997).

Application of apoptin biology has been tested for its efficiency in selectively killing tumor cells in a series of in vitro and in vivo cancer models. Thus far, apoptin has shown a beneficial apoptosis-inducing effect pre-clinically in the context of hepato-carcinoma, breast carcinoma, lung cancer, liver cancer and prostate cancer. Exposing tumor cells to apoptin resulted in a slowdown of tumor growth or even a complete regression of tumors, when delivered to cancer cells intra-tumoral via a non-replicative adenovirus, for the treatment of hepatoma (when part of the Fowl-pox virus genome) (Li et al., *Int. J. Cancer*, 2006). Beneficial effects of apoptin treatment were also reported for Lewis lung carcinoma, when delivered to the aberrant cells as part of plasmid DNA and for hepato-carcinoma, when applying the Asor-DNA delivery approach. For lung tumors, cervix carcinomas, gastric cancer and hepato-carcinomas, apoptin proved effective when recombinant apoptin was used complexed with a polypeptide for tunneling apoptin into targeted cells, i.e., the protein transfer domain TAT protein of HIV or PTD4. Apoptin was beneficial in the treatment of osteosarcoma and prostate cancer, when combined in combinatorial therapeutic approaches (Olijslagers et al., *Basic Clin. Pharmacol. Toxicol.*, 2007). On the other side, apoptin has been proven to be inactive regarding its apoptosis-inducing activity in normal lymphoid cells, dermal cells, epidermal cells, endothelial cells and smooth muscle cells, providing further insight in the cancer cell specificity of apoptin (Danen-van Oorschot et al. 1997).

Apoptin, comprising 121 amino-acid residues, consists of proline-rich regions, two basic C-terminal clusters K82-R89 and R111-R120 and, over all, contains a high percentage of serine and threonine residues. The two basic clusters comprise the apoptin nuclear localization signal in the apoptin 81-121 amino-acid residues fragment. These clusters Ruin a tumor-selective apoptosis domain, regulated by phosphorylation of threonine residue 108 (additionally, apoptin comprises four serine phosphorylation sites in total). A second tumor-selective apoptosis domain is located at the N-teiininus of apoptin and is a hydrophobic domain, involved in apoptin multimerization (apoptin amino-acid residues 1-69) and comprising interaction sites for other, possibly numerous proteins. Multimerization of apoptin results in protein globules, predominantly spherical in shape, consisting of approximately 30 apoptin molecules each. These homogenous oligomerized apoptin globules have tumor-selective apoptosis-inducing activity. The apoptin is approximately 30 mers and can be soluble in nature, or can be insoluble.

Based on the secondary structure prediction results of five different algorithms, feeding the algorithms with the full-length apoptin sequence 1-121 (SEQ ID NO:3), the apoptin amino-acid sequence $^{32}$Glu-Leu$^{46}$ (e.g., amino acids 32-46 of SEQ ID NO:3) encompasses two predicted beta-strands: $^{32}$Glu-Ile-Arg-Ile$^{35}$ (amino acids 32-35 of SEQ ID NO:3) and $^{40}$Ile-Thr-Ile-Thr-Leu-Ser$^{45}$ (amino acids 40-45 of SEQ ID NO:3), of which the latter is possibly extended with $^{39}$Gly and/or with Leu$^{46}$. Circular dichroism spectropolarimetry experiments with an apoptin-His6 construct indeed revealed that apoptin multimers built up of approximately 30 mers have adopted beta-sheet secondary structure to a small extent. The consensus beta-strands allow for formation of an anti-parallel intra-molecular beta-sheet in apoptin molecules. This beta-sheet encompasses two beta-strands: strand a, residues $^{32}$-Glu-Ile-Arg-Ile-$^{35}$ (amino acids 32-35 of SEQ ID NO:3), and strand b, residues $^{40}$-Ile-Thr-Ile-Thr-$^{43}$ (amino acids 40-43 of SEQ ID NO:3), linked by residues $^{36}$-Gly-Ile-Ala-Gly-$^{39}$ (amino acids 36-39 of SEQ ID NO:3). Amino-acid residues Ile33, Ile35, Ile40 and Ile42 form a hydrophobic face at one side of the intra-molecular beta-sheet; Glu32, Arg34, Thr41 and Thr43 form a charged and hydrophilic opposite face of the same beta-sheet. Thus, hydrophobic side chains of all Ile residues are located at one side of the beta-sheet, with all hydrophilic and charged side chains pointing outward at the opposite side of the anti-parallel beta-sheet. With eight amino acid residues in beta-sheet conformation in apoptin 30-mer globules, in theory, 6.6% beta-sheet content could be determined with a CD measurement. With a hydrophobic face and a charged/hydrophilic face, protein surfaces are formed at apoptin that are accessible for incorporation in an inter-molecular amyloid-like structure build up by, apparently, approximately 30 apoptin molecules. The hydrophobic beta-sheet faces of apoptin molecules will form binding interactions and the hydrophilic/charged beta-sheet faces of apoptin molecules will form binding interactions. It appears that the formation of amyloid-like structure resulting in approximately 30 mers is an intrinsic capacity of apoptin related to its tumor-specific apoptosis-inducing activity in transformed and aberrant cells.

In an earlier application (WO02/079222, Fusion proteins for specific treatment of cancer and auto-immune diseases), a polypeptide complex is disclosed with apoptosis-inducing activity and a viral vector comprising the nucleic acid encoding this polypeptide that achieves the goal of (specifically) killing aberrant cells, e.g., tumor cells, by targeting these cells and, as a result, specifically inducing apoptosis in these tumor cells. It is believed that this eradication of aberrant cells is the result of uptake of the polypeptide or of the viral vector bearing the nucleic acid encoding this polypeptide bearing apoptosis-inducing activity, by both aberrant cells and non-transfoimed healthy cells, followed by selective induction of apoptosis in the aberrant cells only, leaving the healthy cells basically unaltered.

SUMMARY OF THE DISCLOSURE

Provided is a proteinaceous molecule comprising at least a domain that comprises an amino acid sequence that specifically binds to an MHC-peptide complex functionally connected with a substance that induces apoptosis in aberrant cells, but not normal cells. In a second embodiment, the substance in the proteinaceous molecule hereof is an apoptosis-inducing polypeptide or protein. In yet another embodiment, the apoptosis-inducing polypeptide or protein and the domain are linked via peptide bonds. In a further embodiment, the apoptosis-inducing polypeptide or protein and the domain comprise a single polypeptide chain. In a preferred embodiment, a proteinaceous molecule is provided wherein the domain specifically binds an MHC-1-peptide complex. In another embodiment, provided is a proteinaceous molecule comprising at least a domain that comprises an amino acid sequence that specifically binds to an MHC-peptide complex functionally connected with a substance that induces apoptosis in aberrant cells, but not normal cells, wherein the peptide within the MHC-peptide complex comprises a MAGE peptide. In a further embodiment, the proteinaceous molecule comprises a substance that induces apoptosis is provided, wherein the substance is apoptin or a fragment and/or derivative thereof, being capable of inducing apoptosis in aberrant cells, but not normal cells. In one embodiment, the proteinaceous molecule comprises the substance in which the substance is a statin. In another embodiment, provided is a proteinaceous molecule comprising at least a domain that comprises an amino acid sequence that specifically binds to an MHC-peptide complex functionally connected with a substance that induces apoptosis in aberrant cells, but not normal cells, wherein the domain is linked to the substance through a non-peptidic bond.

It is a goal of the disclosure to address the above-listed limitations related to specificity of apoptosis-inducing activity toward cancer cells. A second goal is to provide a pharmaceutically active molecule that specifically and effectively induces apoptosis and that, at the same time, is manufactured in a less cumbersome manner. In particular, it is a goal of the present invention to specifically and selectively target aberrant cells and induce apoptosis of these aberrant cells, leaving healthy cells essentially unaffected. MHC-1-peptide complexes on tumors of almost any origin are valuable targets, whereas MHC-2-peptide complexes are valuable targets on tumors of hematopoietic origin.

Thus, provided is a polypeptide comprising a binding domain specifically binding to a certain MHC-p complex exposed on the surface of an aberrant cell and a polypeptide specifically inducing apoptosis (programmed cell death) in this aberrant cell. Preferably, the binding domain and the polypeptide in the fused polypeptide are separated by a linker amino acid sequence. Typically herein, a single polypeptide comprising the necessary binding domain and the necessary apoptosis-inducing polypeptide separated by an amino acid sequence is provided. This does not mean that every molecule hereof may only consist of a single polypeptide chain. It is, e.g., possible to provide one or more connected binding domains for another polypeptide chain on the polypeptide hereof comprising the binding domain and the apoptosis-inducing polypeptide. The third polypeptide would typically not comprise one or more coupled copies of an antibody binding domain and/or an apoptosis-inducing domain like the binding domain and the apoptosis-inducing polypeptide. The third polypeptide would be a polypeptide/protein conferring other desirable properties on the binding and apoptosis-inducing polypeptide, such as improved half-life. As an example, the addition of human serum albumin (HSA) on the polypeptide of the invention may be useful for extension of half-life, etc.

Thus, in one embodiment, a proteinaceous molecule is provided comprising at least a binding domain specific for an MHC-peptide complex functionally connected with a substance that induces apoptosis in aberrant cells, but not noimal cells. Preferably, the one or more binding domains and the substance are functionally connected to each other via peptide bonds between amino-acid residues flanking the binding domain(s) and flanking the substance, providing a linear single-chain proteinaceous molecule. It is also part hereof that the one, two, three and, more preferably, four, five, six or more binding domains are linked to the substance via bonds and/or binding interactions other than covalent peptide bonds between amino acid residues in a linear sequence. Alternative methods for linking proteinaceous molecules to each other are numerous and well known to those skilled in the art of protein linkage chemistry. Protein linkage chemistry not based on peptide bonds in a single-chain amino acid sequence can be based on covalent interactions and/or on non-covalent interactions.

Not intending to be bound to theory, it appears that the aberrant cell-specific apoptosis-inducing activity of the polypeptide hereof results from the specific binding of this polypeptide to surface exposed antigens on aberrant cells. The binding domain of the polypeptide hereof recognizes the complex of MHC-1 loaded with the relevant antigenic peptide present on the targeted aberrant cell exposing the MHC-p complex. The invention is, however, equally applicable with MHC-2. In several occasions, the MHC-p complex is not uniquely exposed by aberrant cells, though predominantly exposed by aberrant cells. It is part hereof that the binding domain of the polypeptide hereof recognizes a selected MHC-1-p complex that is predominantly exposed by the targeted aberrant cell.

Many binding domains able to specifically bind to MHC-p complexes are well known to people of skill in the art. Immediately apparent are binding domains derived from the immune system, such as TCR domains and immunoglobulin (Ig) domains. Preferably, the domains encompass 100 to 150 amino acid residues. Preferably, the binding domains used herein are similar to variable domains ($V_H$ or $V_L$) of antibodies. A good source for such binding domains are phage display libraries. Whether the binding domain of choice is actually physically selected from a library or whether only the information (sequence) is used, is of little relevance. It is part hereof that the polypeptide preferably encompasses one, two, three or more variable domains of antibodies ("multivalency"), linked through peptide bonds with suitable linker sequences. Classical foimats of antibodies such as Fab, whole IgG and single-chain Fv (linked with, e.g., apoptin) against MHC-peptide complexes are also within the scope of the invention.

More and more proteins with apoptosis-inducing activity specific for aberrant cells become known in the art. As part hereof, proteins with apoptosis-inducing activity originating from oncolytic viruses or from other sources can be selected. Preferably, the 121-amino-acid residue apoptin from CAV is used herein.

The techniques of connecting one or multiple connected binding domains with an apoptosis-inducing polypeptide into a single molecule or polypeptide are many and well known.

The single binding domain or the multiple binding domains and the apoptosis-inducing polypeptide on the polypeptide are typically separated by a linker sequence. In many instances, a simple Gly-Ser linker of 4 to 15 amino-acid residues may suffice, but if greater flexibility of the amino-acid chain is desired, longer or more complex linkers may be used. Preferred linkers are $(Gly_4Ser)_n$ (SEQ ID NO:4), (GSTSGS)n (SEQ ID NO:5), GSTSGSGKPGS-GEGSTKG (SEQ ID NO:6), EFAKTTAPSVYPLAPV-LESSGSG (SEQ ID NO:7), or any other linker that provides flexibility for protein folding, stability against protease and flexibility for the polypeptide to exhibit its dual activity, i.e., specific binding to aberrant cells and subsequently specifically inducing apoptosis of the targeted aberrant cells after uptake of at least the apoptosis-inducing polypeptide of the polypeptide. Another group of preferred linkers are linkers based on hinge regions of immunoglobulins. These linkers tend to be quite flexible and quite resistant to proteases. Examples are given in the experimental part. The most preferred linkers are EPKSCDKTHT (SEQ ID NO:8) (IgG1), ELKTPLGDTTHT (SEQ ID NO:9) (IgG3), and ESKYGPP (SEQ ID NO:10) (IgG4). The binding domain(s) and the apoptosis-inducing polypeptide may be separated only by a linker. Alternatively, other useful amino-acid sequences may be introduced between the binding domain(s) and/or between the binding domain(s) and the apoptosis-inducing polypeptide, and/or at the N-tenninus and/or at the C-terminus of the polypeptide of the invention.

As stated before, the binding domains selected according to the invention are preferably based on, or derived from, an Ig domain (or a comparable TCR domain or another binding protein). The Ig domain should have at least one complementarity-determining region (CDR)-like domain or amino-acid sequence, however, preferably three. These CDR-like domains or amino-acid sequences should be separated by framework domains that present the CDR-like stretches in a proper manner. A suitable domain is a $V_H$ domain of a human antibody.

The human $V_H$ domains generally need improvement regarding their affinity and stability, especially when they are derived from Fab or ScFv phage libraries. Thus, solubility engineering steps that transform human $V_H$ domains into soluble non-aggregating, functional entities are part of the present invention. The human $V_H$ domain may be "camelized," meaning that a number of amino-acid residues has been replaced by amino-acid residues from camelids, such as is present in the llama Vhh domain. Preferred substitutions are Glu6Ala, Ala33Cys், Vα137Phe, Gly44Glu, Leu45Arg, Trp47Gly, Ser74Ala, Arg83Lys, Ala84Pro, Trp103Arg or Leu108Gln. Amongst other improvements, introduction of these preferred amino-acid residue substitutions in the human Vh sequence improves the solubility and improves the capability to reverse thermal denaturation. Thus, provided is a polypeptide hereof, wherein the specific binding domains comprise an Ig fragment. The origin or the method of selection, as well as the method of production, of the Ig fragment to be used in the polypeptide is not really relevant. According to one embodiment, a polypeptide comprises an Ig fragment, which is a natural, mutated and/or synthetic VH.

Although the disclosure contemplates many different combinations of MHC and antigenic peptides, the most preferred is the combination of MHC-1 and an antigenic peptide from a tumor-related antigen presented by MHC-1. Because of HLA restrictions, there are many combinations of MHC-1-p complexes, as well as of MHC-2-p complexes, that can be designed based on the rules for presentation of peptides in MHC. These rules include size limits on peptides that can be presented in the context of MHC, restriction sites that need to be present for processing of the antigen in the cell, anchor sites that need to be present on the peptide to be presented, etc. The exact rules differ for the different HLA classes and for the different MHC classes. It is found that MAGE-derived peptides are very suitable for presentation in an MHC context. An MHC-1-presentable antigenic peptide with the sequence Y-L-E-Y-R-Q-V-P-G (SEQ ID NO:11) in MAGE-A was identified, that is present in almost every MAGE-A variant and that will be presented by one of the most prevalent MHC-1 alleles in the Caucasian population (namely HLA-A0201). A second MAGE peptide that is presented by another MHC-1 allele (namely HLA-CW7) and that is present in many MAGE variants, like, for example, MAGE-A2, -A3, -A6 and -A12, is E-G-D-C-A-P-E-E-K (SEQ ID NO:12). These two combinations of MHC-1 and MAGE peptides together could cover 80% of the Caucasian population. It has been shown in vitro that tumor cell lines with the correct HLA alleles present are efficiently killed when the MHC-1-p complex is targeted by a hexavalent complex of VH domain non-covalent multimers specific for this MHC-1-p complex (see international publication WO2007/073147). The same approach can be followed for other MHC molecules, other HLA restrictions and other antigenic peptides derived from tumor-associated antigens. Relevant is that the chosen antigenic peptide to elicit the response must be presented in the context of an MHC molecule and recognized in that context only. Furthermore, the antigenic peptide must be derived from a sufficiently tumor-specific antigen and the HLA restriction must occur in a relevant part of the population. One of the important advantages of the present invention is that tumors that down-regulate their targeted MHC-peptide complex, can be treated with a second binding molecule comprising at least one binding domain binding to a different MHC-peptide complex based on the same antigen. If this one is down-regulated, a third one will be available. Six different targets on MHC may be available. Since cells need to be "inspected" by the immune system from time to time, escape through down-regulation of all MHC molecules does not seem a viable escape route. In the case that MAGE is the antigen from which the peptide is derived, escape through down-regulation of the antigen is also not likely, because MAGE seems important for survival of the tumor (L. Marcar et al., *Cancer Res.* 2010, 70:10362-10370). Thus, the present invention, in an important aspect, reduces or even prevents escape of the tumor from the therapy, in the sense that the tumor remains treatable.

Because one embodiment uses MHC molecules as a target and individuals differ in the availability of MHC targets, also provided is a so-called companion diagnostic to determine the HLA composition of an individual. Although the disclosure preferably uses a more or less universal (MAGE) peptide, it also provides a diagnostic for determining the expression of the particular antigen by the tumor. In this manner, the therapy can be geared to the patient, particularly also in the set-up to prevent escape as described hereinbefore. It is known that the HLA restriction patterns of the Asian population and the black population are different from the Caucasian population. For these populations, different MHC-peptide complexes can be targeted, as described in the detailed description.

Although the present specification presents more specific disclosure on tumors, it must be understood that other aberrant cells can also be targeted by the polypeptides of the present invention. These other aberrant cells are typically cells that also proliferate without sufficient control. This occurs in autoimmune diseases. It is typical that these cells start to show expression of tumor antigens. In particular, MAGE polypeptides have been identified in Rheumatoid Arthritis (D. K. McCurdy et al., *J. Rheumatol.* 2002, 29:2219-2224). Thus, provided in a preferred embodiment, a polypeptide wherein the specific binding domain is capable of binding to an MHC-1-p complex and is covalently bound to an apoptosis-inducing polypeptide. In a further preferred embodiment, provided is a polypeptide wherein the specific binding domain is capable of binding to MHC-1-p complexes comprising an antigenic peptide derived from a tumor-related antigen, in particular, MHC-1-p complexes comprising an antigenic peptide present in a variety of MAGE antigens, covalently bound to an apoptosis-inducing polypeptide.

One of the polypeptides exemplified herein has a single binding domain with the amino-acid sequence, referred to as Vh, essentially corresponding to: the first 117 amino acids of SEQ ID NO:2).

Another one has at least one binding domain comprising the amino acid sequence: EVQLVQSGGGLVKPGGSL-RLSCAASGFTFSDYYMSWIRQAPGKGLEWLSYIS SDGSTIYYADSVKGRFTVSRDNAKNSLSLQMNSL-RADDTAVYYCAVSPRGYYYYGLDL WGQGTTVTVSS (SEQ ID NO:13; 11H).

One of the polypeptides exemplified herein has two binding domains with the amino-acid sequence, referred to as (Vh)$_2$, essentially corresponding to: MAQLQLQESGGGVVQPGRSLRLSCAASGFTF-SSYGMHWVRQAPGKEREGVAVISYDGS NKYYADS-VKGRFTISRDNSKNTLYLQMNSLRAEDTAVYYCA-GGSYYVPDYWGQGTLV TVSS (SEQ ID NO:14)—linker amino-acid sequence—QLQLQESGGGVVQPGRSLRL SCAASGFTFSSYGMHWVRQAPGKEREGVAVISYDG-SNKYYADSVKGRFTISRDNSKNT LYLQMNSLRAED-TAVYYCAGGSYYVPDYWGQGTLVTVSS (SEQ ID NO:15), with, for example, the linker amino-acid sequence GGGGSGGGGS (SEQ ID NO:16) and two AH5 Vh binding domains.

One of the polypeptides exemplified herein has three binding domains with the amino-acid sequence, referred to as (Vh)$_3$, essentially corresponding to: MAQLQLQESGGGVVQPGRSLRLSCAASGFTF-SSYGMHWVRQAPGKEREGVAVISYDGS NKYYADS- VKGRFTISRDNSKNTLYLQMNSLRAEDTAVYYCAGGSYYVPDYWGQGTLV TVSS (SEQ ID NO:14)—linker amino-acid sequence—QLQLQESGGGVVQPGRSLRLSCAAS GFTFSSYGMHWVRQAPGKEREGVAVISYDGSNKYYADSVKGRFTISRDNSKNTLYLQM NSLRAEDTAVYYCAGGSYYVPDYWGQGTLVTVSS (SEQ ID NO:15)—linker amino-acid sequence—QLQLQESGGGVVQPGRSLRLSCAASGFTFSSYGMHWVRQAPGKEREGVAV ISYDGSNKYYADSVKGRFTISRDNSKNTLYLQMNSLRAEDTAVYYCAGGSYYVPDYW GQGTLVTVSS (SEQ ID NO:15), with, for example, the linker amino-acid sequences GGGGSGGGGS (SEQ ID NO:16) and three AH5 Vh binding domains.

One of the polypeptides exemplified herein has four binding domains with the amino-acid sequence, referred to as (Vh)$_4$, essentially corresponding to: MAQLQLQESGGGVVQPGRSLRLSCAASGFTFSSYGMHWVRQAPGKEREGVAVISYDGS NKYYADSVKGRFTISRDNSKNTLYLQMNSLRAEDTAVYYCAGGSYYVPDYWGQGTLV TVSS (SEQ ID NO:14)—linker amino-acid sequence—QLQLQESGGGVVQPGRSLRLSCAAS GFTFSSYGMHWVRQAPGKEREGVAVISYDGSNKYYADSVKGRFTISRDNSKNTLYLQM NSLRAEDTAVYYCAGGSYYVPDYWGQGTLVTVSS (SEQ ID NO:15)—linker amino-acid sequence—QLQLQESGGGVVQPGRSLRLSCAASGFTFSSYGMHWVRQAPGKEREGV AVISYDGSNKYYADSVKGRFTISRDNSKNTLYLQMNSLRAEDTAVYYCAGGSYYVPDY WGQGTLVTVSS (SEQ ID NO:15)—linker amino-acid sequence—QLQLQESGGG VVQPGRSLRLSCAASGFTFSSYGMHWVRQAPGKEREGVAVISYDGSNKYYADSVKGRF TISRDNSKNTLYLQMNSLRAEDTAVYYCAGGSYYVPDYWGQGTLVTVSS (SEQ ID NO:15), with, for example, the linker amino-acid sequences GGGGSGGGGS (SEQ ID NO:16) and four AH5 Vh binding domains.

One of the polypeptides exemplified herein has an apoptosis-inducing polypeptide with the amino-acid sequence, referred to as apoptin, essentially corresponding to: MNALQEDTPPGPSTVFRPPTSSRPLETPHCREIRIGIAGITITLSLCGCANARAPTLRSATA DNSESTGFKNVPDLRTDQPKPPSKKRSCDPSEYRVSELKESLITTTPSRPRTAKRRIRL (SEQ ID NO:3).

Preferred polypeptides according to the invention have an amino-acid sequence, referred to as Vh-apoptin, essentially corresponding to MAQLQLQESGGGVVQPGRSLRLSCAASGFTFSSYGMHWVRQAPGKEREGVAVISYDGSNKYYADSVKGRFTISRDNSKNT LYLQMNSLRAEDTAVYYCAGGSYYVPDYWGQGTLVTVSS (SEQ ID NO:14)—linker amino-acid sequence—NALQEDTPPGPSTVFRPPTSS RPLETPHCREIRIGIAGITITLSLCGC ANARAPTLRSATADNSESTGFKNVPDLRTDQPKPPSKKRSCDPSEYRVSELKESLITTTPS RPRTAKRRIRL (SEQ ID NO:17), referred to as (Vh)$_1$-apoptin or AH5-apoptin, with, for example, the linker amino-acid sequences GGGGSGGGGS (SEQ ID NO:16) and one AH5 Vh binding domain or to MAQLQLQESGGGVVQPGRSLRLSCAASGFTFSSYGM HWVRQAPGKEREGVAVISYDGSNKYYADSVKGRFTISRDNSKNTLYLQMNSLRAEDTA VYYCAGGSYYVPDYWGQGTLVTVSS (SEQ ID NO:14)—linker amino-acid sequence—QLQLQESGGGVVQPGRSLRLSCAASGFTFS SYGMHWVRQAPGKEREGVAVISYDGSNK YYADSVKGRFTISRDNSKNTLYLQMNSLRAEDTAVYYCAGGSYYVPDYWGQGTLVTV SS (SEQ ID NO:15)—linker amino-acid sequence—NALQEDTPPGPSTVFRPPTSS RPLETPHCREIRIGIAGITITLSLCGCANARAPTLRSATADNSESTGFKN VPDLRTDQPKPP SKKRSCDPSEYRVSELKESLITTTPSRPRTAKRRIRL (SEQ ID NO:17), referred to as (Vh)$_2$-apoptin, with, for example, the linker amino-acid sequences GGGGSGGGGS (SEQ ID NO:16) and two AH5 Vh binding domains or to MAQLQLQESGGGVVQPGRSLRLSCAAS GFTFSSYGMHWVRQAPGKEREGVAVISYDGSNKYYADSVKGRFTISRDNSKNTLYLQM NSLRAEDTAVYYCAGGSYYVPDYWGQGTLVTVSS (SEQ ID NO:14)—linker amino-acid sequence—QLQLQESGGGVVQPGRSLRLSCAASGFTFSSYGMHWVRQAPGKEREGVA VISYDGSNKYYADSVKGRFTISRDNSKNTLYLQMNSLRAEDTAVYYCAGGSYYVPDY WGQGTLVTVSS (SEQ ID NO:15)—linker amino-acid sequence—QLQLQESGGGVV QPGRSLRLSCAASGFTFS SYGMHWVRQAPGKEREGVAVISYDGSNKYYADSVKGRFTIS RDNSKNTLYLQMNSLRAEDTAVYYCAGGSYYVPDYWGQGTLVTVSS (SEQ ID NO:15)—linker amino-acid sequence—NALQEDTPPGPSTVFRPPTSSRPLETPH CREIRIGIAG ITITLSLCGCANARAPTLRSATADNSESTGFKNVPDLRTDQPKPPSKKRSCDPSEYRVSEL KESLITTTPSRPRTAKRRIRL (SEQ ID NO:17), referred to as (Vh)$_3$-apoptin, with, for example, the linker amino-acid sequences GGGGSGGGGS (SEQ ID NO:16) and three AH5 Vh binding domains or to MAQLQLQESGGGVVQPGRSLRLSCAASGFTFSSYGMH WVRQAPGKEREGVAVISYDGSNKYYADSVKGRFTISRDNSKNTLYLQMNSLRAEDTAV YYCAGGSYYVPDYWGQGTLVTVSS (SEQ ID NO:14)—linker amino-acid sequence—QLQLQESGGGVVQPGRSLRLSCAASGFTFSSYGMHWVRQAPGKEREGVAVISYDGSNK YYADSVKGRFTISRDNSKNTLYLQMNSLRAEDTAVYYCAGGSYYVPDYWGQGTLVTV SS (SEQ ID NO:15)—linker amino-acid sequence—QLQLQESGGGVVQPGRSLRLS CAASGFTFSSYGMH WVRQAPGKEREGVAVISYDGSNKYYADSVKGRFTISRDNSKNTL YLQMNSLRAEDTAVYYCAGGSYYVPDYWGQGTLVTVSS (SEQ ID NO:15)—linker amino-acid sequence—QLQLQESGGGVVQPGRSLRLSCAAS GFTFS SYGMHWVRQAPGK EREGVAVISYDGSNKYYADSVKGRFTISRDNSKNTLYLQMNSLRAEDTAVYYCAGGSY YVPDYWGQGTLVTVSS (SEQ ID NO:15)—linker amino-acid sequence—NALQED TPPGPSTVFRPPTSSRPLETPHCREIRIGIAGITITLSLCGCANARAPTLRSATADNSESTGF KNVPDLRTDQPKPPSKKRSCDPSEYRVSELKESLITTTPSRPRTAKRRIRL (SEQ ID NO:17), referred to as (Vh)$_4$-apoptin, with, for example, the linker amino-acid sequences GGGGSGGGGS (SEQ ID NO:16) and four AH5 Vh binding domains.

Preferred polypeptides according to the invention have an amino-acid sequence including a cathepsin-L cleavage site (RKELVTPARDFGHFGLS) (SEQ ID NO:18), referred to as Vh-cath-apoptin, essentially corresponding to: MAQLQLQESGGGVVQPGRSLRLSC AASGFTFSSYGMHWVRQAPGKEREGVAVISYDGSNKYYADSVKGRFTISRDNSKNTLY LQMNSLRAEDTAVYYCAGGSYYVPDYWGQGTLVTVSS (SEQ ID NO:14)—linker amino-acid sequence—RKELVTPARDFGHFGLSNALQEDTPPGPSTVFRPPTSSRPLETPH CREIRIGIAGITITLSLCGCANARAPTLRSATADNSESTGFKN VPDLRTDQPKPPSKKRSCD PSEYRVSELKESLITTTPSRPRTAKRRIRL (SEQ ID NO:19), referred to as (Vh)$_1$-cath-apoptin, with, for example, the linker amino-acid sequences GGGGSGGGGS (SEQ ID NO:16) and one AH5 Vh binding domain or to MAQLQLQESGGGVV QPGRSLRLSCAASGFTF- SSYGMHWVRQAPGKEREGVAVISYDGSNKYYADS-VKGRFTIS RDNSKNTLYLQMNSLRAEDTAVYYCA-GGSYYVPDYWGQGTLVTVSS (SEQ ID NO:14)—linker amino-acid sequence—QLQLQESGGGVVQPGRSLRLS-CAASGFTFSS YGMHWVRQAPGKEREGVAVISYDG-SNKYYADSVKGRFTISRDNSKNTLYLQMNSLRA EDTAVYYCAGGSYYVPDYWGQGTLVTVSS (SEQ ID NO:15)—linker amino-acid sequence RKELVTPARDFGH-FGLSNALQEDTPPGPSTVFRPPTSSRPLETPHCREIRI-GIAGITITLSL CGCANARAPTLRSATADNSESTGFKN-VPDLRTDQPKPPSKKRSCDPSEYRVSELKESLIT TTPSRPRTAKRRIRL (SEQ ID NO:19), referred to as (Vh)$_2$-cath-apoptin, with, for example, the linker amino-acid sequences GGGGSGGGGS (SEQ ID NO:16) and two AH5 Vh binding domains or to MAQLQLQESGGGV-VQPGRSLRLSCAASGFTFSSYGMHWVRQAPGK-EREG VAVISYDGSNKYYADSVKGRFTISRDNSKNT-LYLQMNSLRAEDTAVYYCAGGSYYVPD YWGQGTLVTVSS (SEQ ID NO:14) \—linker amino-acid sequence—QLQLQESGGG VVQPGRSLRLSCAAS-GFTFSSYGMHWVRQAPGKEREGVAVISYDGSNKYY-ADSVKGRF TISRDNSKNTLYLQMNSLRAED-TAVYYCAGGSYYVPDYWGQGTLVTVSS (SEQ ID NO:15) \—linker amino-acid sequence—QLQLQESGGGVVQPGRSLRLSCAASGFTFSSY GMH-WVRQAPGKEREGVAVISYDGSNKYYADSVKGR-FTISRDNSKNTLYLQMNSLRAE DTAVYYCAGGSYYVPDYWGQGTLVTVSS (SEQ ID NO:15) \—linker amino-acid sequence RKELVTPARDF-GHFGLSNALQEDTPPGPSTVFRPPTSSRPLETPH-CREIRIGIAGITITLSL CGCANARAPTLRSATADNSES-TGFKNVPDLRTDQPKPPSKKRSCDPSEYRVSELKESLIT TTPSRPRTAKRRIRL (SEQ ID NO:19), referred to as (Vh)$_3$-cath-apoptin, with, for example, the linker amino-acid sequences GGGGSGGGGS (SEQ ID NO:16) and three AH5 Vh binding domains or to MAQLQLQESGGGV-VQPGRSLRLSCAASGFTFSSYGMHWVRQAPGK-EREG VAVISYDGSNKYYADSVKGRFTISRDNSKNT-LYLQMNSLRAEDTAVYYCAGGSYYVPD YWGQGTLVTVSS (SEQ ID NO:14)—linker amino-acid sequence—QLQLQESGGG VVQPGRSLRLSCAAS-GFTFSSYGMHWVRQAPGKEREGVAVISYDGSNKYY-ADSVKGRF TISRDNSKNTLYLQMNSLRAED-TAVYYCAGGSYYVPDYWGQGTLVTVSS (SEQ ID NO:15)—linker amino-acid sequence—QLQLQESGGGV-VQPGRSLRLSCAASGFTFSS YGMHWVRQAPGK-EREGVAVISYDGSNKYYADSVKGRFTISRDNSKNT-LYLQMNSLRA EDTAVYYCAGGSYYVPDYWGQGTLVTVSS (SEQ ID NO:15)—linker amino-acid sequence—QLQLQESGGGV-VQPGRSLRLSCAASGFTFSSYGMHWVRQAPGK-EREGVAVISYDGS NKYYADSVKGRFTISRDNSKNT-LYLQMNSLRAEDTAVYYCAGGSYYVPDYWGQGTLV TVSS (SEQ ID NO:15)—linker amino-acid sequence—RKELVTPARDFGHFGLSNAL QEDTPPGPSTV-FRPPTSSRPLETPHCREIRIGIAGITITLSLCGCA-NARAPTLRSATADNSES TGFKNVPDLRTDQPKPPSKKRSCDPSEYRVSEL-KESLITTTPSRPRTAKRRIRL (SEQ ID NO:19), referred to as (Vh)$_4$-cath-apoptin, with, for example, the linker amino-acid sequences GGGGSGGGGS (SEQ ID NO:16) and four AH5 Vh binding domains.

Equally preferred are polypeptides hereof similar to those listed above, now comprising Vh binding domain 11H instead of AH5. It is appreciated that additional preferred constructs according to the invention have other cleavage sites such as, but not limited to, e.g., the cathepsin-B cleavage site with sequence GFQGVQFAGF (SEQ ID NO:20). Even more preferred constructs comprising consecutive binding domains comprise different preferred linker amino-acid sequences between a first and a second binding domain, and a second, a third and a fourth binding domain. In the above-outlined examples of polypeptides, the apoptosis-inducing polypeptide or protein is positioned at the C-terminal site of the one or more binding domains. Polypeptides with the apoptosis-inducing polypeptide or protein, like, for example, apoptin, positioned at the N-terminal site of the one or more binding domains are also part hereof. See also FIG. 5 for examples of preferred molecules hereof.

The disclosure comprises the nucleic acids encoding the polypeptides. The molecules can be produced in prokaryotes as well as eukaryotes (one has to take care because apoptin induces cell death in cell lines (which are essentially tumor cells)). The codon usage of prokaryotes may be different from that in eukaryotes. The nucleic acids can be adapted in these respects. Also, elements that are necessary for secretion may be added, as well as promoters, terminators, enhancers, etc. Also, elements that are necessary and/or beneficial for the isolation and/or purification of the polypeptides may be added. Typically, the nucleic acids are provided in an expression vector suitable for the host in which they are to be produced. Choice of a production platform will depend on the size of the molecule, the expected issues around protein folding, whether additional sequences are present that require glycosylation, expected issues around isolation and/or purification, etc. Thus, nucleic acids according to the invention are typically adapted to the production and purification platform in which the polypeptides according to the invention are to be produced. Thus, provided is a nucleic acid encoding a polypeptide according to the disclosure, as well as an expression vector comprising such a nucleic acid. For stable expression in a eukaryote, it is preferred that the nucleic acid encoding the polypeptide be integrated in the host cell genome (at a suitable site that is not silenced). Thus, the disclosure comprises in a particular embodiment, a vector comprising means for integrating the nucleic acid in the genome of a host cell.

The disclosure further comprises the host cell or the organism in which the polypeptide-encoding nucleic acid is present and which is thus capable of producing the polypeptide according to the invention.

Included herein are also the methods for producing a polypeptide hereof, comprising culturing a host cell comprising a suitbable nucleic acid, allowing for expression of the nucleic acid and harvesting the polypeptide.

For administration to subjects, the polypeptide is formulated. Typically, these polypeptides will be given parenterally. For foimulation, simply water (saline) for injection may suffice. For stability reasons, more complex formulations may be necessary. The disclosure contemplates lyophilized compositions as well as liquid compositions, provided with the usual additives. Thus, provided is a pharmaceutical composition comprising a polypeptide complex according to the disclosure and suitable diluents and/or excipients.

The dosage of the polypeptides according to the invention must be established through animal studies and clinical studies in so-called rising-dose experiments. Typically, the doses will be comparable with present day antibody dosages (at the molar level, the molecular weight of the molecules may differ from that of antibodies). Typically, such dosages are 3-15 mg/kg body weight, or 25-1000 mg per dose.

It has been established in the field of tumor therapy that a single agent is hardly ever capable of eradication of a tumor from a patient. Especially in the more difficult to treat tumors, the first applications of the polypeptides hereof will (at least initially) probably take place in combination with other treatments (standard care). Thus, also provided is a pharmaceutical composition comprising a polypeptide and a conventional cytostatic and/or tumoricidal agent. Moreover, also provided is a pharmaceutical composition comprising a polypeptide for use in an adjuvant treatment of cancer. Additionally, provided is a pharmaceutical composition comprising a polypeptide for use in a combination chemotherapy treatment of cancer. Examples of chemotherapeutical treatments that are combined with the pharmaceutical composition are etoposide, paclitaxel and methotrexate.

The pharmaceutical compositions will typically find their use in the treatment of cancer, particularly in forms of cancer where the targets of the preferred single-chain polypeptide (i.e., complexes of MHC and MAGE-A antigenic peptides), are presented by the tumors. Table 1 gives a list of tumors on which these targets have, for example, been found. It is easy using (a) binding domain(s) according to the invention to identify tumors that present the target MHC-p complexes. This can be done in vitro or in vivo (imaging).

The term repeat has the same meaning as domain and motif throughout the specification.

DETAILED DESCRIPTION OF THE INVENTION

Figure 1:
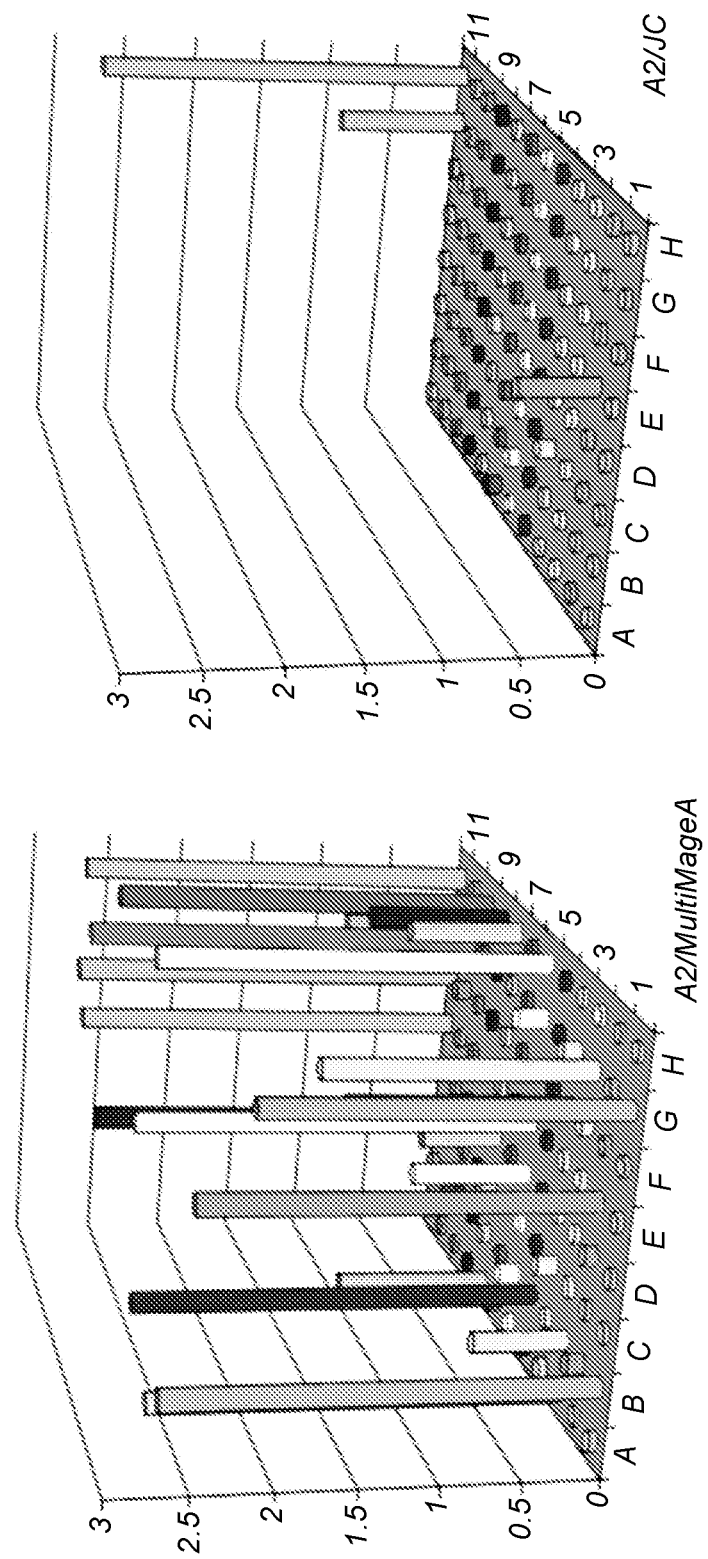
FIG. 1: Specific binding of HLA-A0201/multi-MAGE-A specific phage clones isolated from a large human non-immune antibody Fab phage library. Individual antibody Fab expressing phages that were selected against biotinylated HLA-A0201/multi-MAGE-A were analyzed by ELISA for their capacity to bind the relevant peptide/MHC complex only. Streptavidin-coated 96-well plates were incubated with soluble HLA-A0201/multi-MAGE-A (A2/multi-Mage) or HLA-A0201/JCV (A2/JC) peptide/MHC complexes (10 µg/ml), washed to remove non-bound complexes and incubated with individual phage clones. Non-binding phages were first removed by three washes with PBS/TWEEN®, followed by incubation with anti-M13 antibody (1 µg/ml, Amersham) for one hour by room temperature. Finally, the wells were incubated with an HRP-labeled secondary antibody and bound phages detected.

As outlined in the previous application WO2007/073147, the desired specific and selective killing of aberrant cells via the apoptosis machinery can be achieved by contacting these cells with a multivalent protein complex comprising multiple antigen-specific MHC-restricted TCRs or MHC-restricted antigen-specific antibodies or antibody domains. The antigen then is expressed by the targeted aberrant cells and presented in the context of MHC molecules. This finding then, opened the possibility to selectively kill a population of cells that are positive for a certain MHC-p complex of interest. For example, tumor cells expressing HLA class I molecules in complex with antigenic peptides derived from tumor-associated antigens (MAGE-A1, -A2, -A3, -A4, -A5, -A6, -A7, -A8, -A9, -A10, -A11, -A12, -A12, MAGE-B, MAGE-C2, LAGE-1, PRAME, NY-ESO-1, PAGE, SSX-2, SSX-4, GAGE, TAG-1, TAG-2, and HERV-K-MEL).

In addition, as outlined in our earlier application WO02/079222 (Fusion proteins for specific treatment of cancer and auto-immune diseases), the desired specific and selective killing of aberrant cells via the apoptosis machinery can be achieved by contacting these cells with recombinant apoptosis-inducing apoptin protein. This specific and selective killing can be achieved in one of several ways. For example, when apoptin is fused with a polypeptide such as TAT or PTD4, that adds a signal for cellular uptake to apoptin; or by micro-injecting targeted aberrant cells specifically with recombinant apoptin protein; or, for example, by contacting cells including aberrant cells with non-replicative viruses bearing the apoptin nucleic acid. Once delivered in a non-specific manner to aberrant cells, apoptin exposes its apoptosis-inducing activity specific for transformed and aberrant cells, such as tumor cells. Overcoming the barrier of providing predominantly aberrant cells with this ability of apoptin to trigger their cell-death machinery specifically, efficient and selectively, would open the possibility to develop new generation anti-cancer therapeutics acting on aberrant cells only, thus being able to arrest tumor growth and moreover being able to bring existing tumors into regression.

In the current application, selectivity and affinity for cancer cell-specific antigens were combined with cancer cell-specific apoptosis-inducing activity in a polypeptide of the invention. The present invention thus discloses that the goal of specifically killing aberrant cells can be achieved by providing a polypeptide comprising a polypeptide domain specifically binding to a certain antigen associated with aberrant cells, and comprising a cell death-inducing polypeptide. After uptake of the polypeptide, these aberrant cells are selectively and specifically killed by the apoptosis-inducing activity of the polypeptides. Thus, in a first embodiment, this molecule binds specifically to an antigen unique to aberrant cells, and thereby transfers its ability to selectively induce apoptosis into the targeted aberrant cells. The intracellular delivery of the apoptosis-inducing activity of the molecules into aberrant cells predominantly leaves healthy cells and tissue essentially unaltered, even if targeted to a certain level by the molecules. It is part of the disclosure that the polypeptide is presented as a monomer or as a non-covalent complex of monomers.

The terms protein and polypeptide have roughly the same meaning throughout the text of this application and refer to a linear proteinaceous sequence comprising two or more amino-acid residues. In the context of the proteins, protein domains, and domains that specifically bind to MHC-p complexes, binding molecules, binding domains and polypeptides have the same meaning as proteins.

The term apoptosis refers to the process of programmed cell death. The ten apoptosis-inducing activity means the ability of a protein or a virus or any other polypeptide, compound, organism or molecule according to the current invention, to activate, induce, influence and/or stimulate the cell death machinery of a cell, resulting in the process of programmed cell death. An aberrant cell is defined as a cell that deviates from its usual and healthy normal counterparts in its abnormal growth characteristics.

Apoptin bears tumor cell-specific apoptosis-inducing activity, acts independently of p53 and is, in several tumor cell types, insensitive to Bcr-Abl and Bcl-xl and even stimulated by Bcl-2. These characteristics attribute to the high potency of apoptin when applied in the development of new anti-tumor medicaments according to the invention.

The binding domain that specifically recognizes and binds to an MHC-p complex can be a TCR or a functional fragment thereof (together herein referred to as TCRs) and/or an antibody that mimics TCR specificity, for example, a genetically engineered antibody such as a single-chain variable fragment (scFv) or the variable domain V of the heavy chain H of an antibody (referred to throughout the text as VH, Vh or $V_H$). In the specification, MHC-peptide complex and MHC-peptide antigen have the same meaning. In the context of a peptide that is presented by an MHC molecule, forming an MHC-p complex, the terms peptide, peptidic antigen, antigenic epitope and antigenic peptide refer to the same peptide in the MHC-p complex.

Multivalent TCR domain complexes and therapeutic applications thereof are known in the art. In application WO2004/050705, a multivalent TCR domain complex comprising at least two TCRs, linked by a non-proteinaceous polymer chain or a linker sequence composed of amino-acid residues, is disclosed. The disclosed use of the TCR complex is in targeting cell delivery of therapeutic agents, such as cytotoxic drugs, which can be attached to the TCR complex. Furthermore, WO2004/050705 focuses on the use of a multivalent TCR complex for the delivery of a therapeutic agent, e.g., a toxic moiety for cell killing, to a target cell.

The specific binding capacity of one or multiple MHC-p complex binding domain(s) fused with an apoptosis-inducing polypeptide and rendered with the ability to be taken up specifically by the targeted aberrant cell of the current invention is sufficient to induce apoptosis of a target cell expressing the relevant antigen. Any binding domain capable of specifically binding to an MHC-p complex, comprising either MHC class I or MHC class II proteins, is suitably used in an apoptosis-inducing single-chain polypeptide hereof. Also according to the disclosure, any proteinaceous molecule capable of specifically inducing apoptosis in an aberrant cell is suitably used in an apoptosis-inducing single-chain polypeptide hereof. In one embodiment, therefore, this molecule comprises one or multiple polypeptide binding domains connected through regular peptide bonds comprising an amino acid sequence corresponding to a $V_H$ domain of a human antibody specifically binding to an MHC-p complex, and a polypeptide comprising the amino acid sequence corresponding to apoptin-inducing apoptosis once engulfed by a target cell, connected through peptide bonds between the $V_H$ domain(s) and apoptin.

The terms cancer cell and tumor cell have basically the same meaning throughout the specification.

This disclosure is, like in application WO2007/073147, primarily exemplified by the generation of a single-chain monomeric polypeptide encompassing one $V_H$ domain or multiple $V_H$ domains and apoptin, which is specific for a tumor antigen and which specifically kills tumor cells.

This single-chain monomeric polypeptide has therapeutic value in the treatment of cancer and autoimmune diseases. Moreover, the skilled person will appreciate that it is not limited to any type of antigen, and that single-chain monomeric polypeptides are provided that can selectively kill target cells, like, for example, selected aberrant cells, expressing any antigen, known or still to be discovered, presented in the context of MHC.

Preferably, a molecule hereof is capable of specifically and efficiently recognizing and binding to a cancer-specific epitope or an epitope associated with autoimmune disorders or an epitope presented by any other aberrant cell, for all examples in the context of MHC. Cancer cells may express a group of antigens termed "cancer testis antigens" (CT). These CT are presented as antigenic peptides by MHC molecules to CTLs. In fact, these CT are immunogenic in cancer patients as they may elicit anti-cancer responses. They exhibit highly tissue-restricted expression and are considered promising target molecules for cancer vaccines and other immune intervention strategies.

To date, more than 44 CT gene families have been identified and their expression has been studied in numerous cancer types. For example, bladder cancer, non-small lung cancer, prostate cancer, melanoma and multiple myeloma express CT genes to a high level. Experiments have shown that expression of these CT genes was indeed testis restricted in healthy individuals. Other antigens that were shown to elicit immune responses in cancer patients include differentiation antigens such as, for example, the melanoma antigens gp100, Mart-1, Tyrosinase, or antigens that are over-expressed in cancer cells, such as, for example, p53, Her-2/neu, WT-1. In a preferred embodiment, the polypeptide according to the invention is capable of recognizing and binding to an MHC class I-p complex or to an MHC class II-p complex with the antigenic peptide in the MHC-p complex derived from a tumor antigen, in particular, melanoma-associated antigens, and with the MHC-p complex specifically expressed at tumor cells, leaving healthy cells and tissue essentially unaltered. The general benefit of the disclosure is that, where up until now targets associated with cell surfaces were the predominant goal, intracellular targets now become available through presentation by MHC-1 and/or MHC-2. This means that a renewed survey of intracellular antigens will be carried out to identify intracellular antigens that are tumor specific enough to merit using them as targets in the disclosure. Such a screen has already been carried out in the context of tumor vaccination schemes. Targets that are valuable (because of sufficient specificity, not necessarily efficacy) as tumor vaccine candidates will also be valuable: MAGE-A1, -A2, -A3, -A4, -A5, -A6, -A7, -A8, -A8, -A10, -A11, -A12, MAGE-B, MAGE-C2, LAGE-1, SSX-2, SSX-4, PRAME, PAGE, NY-ESO-1, GAGE, and HERV-K-MEL.

Human tumor antigen-derived antigenic peptides presented by MHC class II molecules have been described, with nearly all of them being associated with multiple myeloma or malignant melanoma. The first melanoma antigenic peptide found was MAGE-1. Furthermore, three melanoma epitopes were found to originate from the MAGE family of proteins and presented by HLA-DR11 and HLA-DR13. Another set of melanoma antigens, known to contain also MHC class I tumor antigens, comprises Melan-A/MART-1, gp100 and Tyrosinase. For an overview of T-cell epitopes that are of use for the present invention, also see the World Wide Web at cancerimmunity.org/peptidedatabase/Tcellepitopes.htm.

The first discovered CT, belonging to the group of MAGE-A antigens, has an expression profile that is uniquely restricted to cancer cells and testis cells. However, testis cells are not targeted by the immune system, as they lack expression of MHC molecules. The MAGE-A antigens belong to a family of twelve genes that show high homology. Their expression has been associated with early events in malignant cell transformation and metastatic spread of cancer cells. In addition, down-regulation of MAGE-A expression may induce apoptosis in cancer cells. Within the MAGE-A genes, several antigenic epitopes are known by persons in the art. Antigenic peptides usually are presented as 8- or 9-mer amino acid peptides by MHC class I molecules. In addition, epitopes are known that are present in multiple MAGE-A genes due to the high homology between the different MAGE-A genes. These epitopes may be considered as multi-MAGE-A epitopes and are presented on cancer cells of various histologic origin. Therefore, they might serve as universal targets for anti-cancer therapy.

MHC molecules are also important as signal-transducing molecules, regulating immune responses. Cross-linking of MHC Class I molecules on B and T cells initiates signals that can result in either anergy, or apoptosis, or, alternatively, in cell proliferation and cytokine production. Several intracellular signaling pathways have been identified that are induced by MHC class I cross-linking. These include 1) phosphorylation of tyrosine kinases, leading to enhanced levels of intracellular calcium ions; 2) activation of the JAK/STAT pathway; and 3) inhibition of PI3K, resulting in the activation of JNK activation. In addition, cross-linking of MHC Class I/II molecules results in the engulfment of the MHC-p complexes with bound single-chain polypeptide according to the invention, allowing the delivery of, e.g., toxic proteins or toxic compounds.

A further aspect relates to a method for providing the molecule hereof. As described hereinabove, it typically involves providing a nucleic acid construct encoding the desired polypeptide. The nucleic acid construct can be introduced, preferably via a plasmid or expression vector, into a prokaryotic host cell and/or in eukaryotic host cell capable of expressing the construct. In one embodiment, a method to provide a single-chain apoptosis-inducing protein comprises the steps of providing a host cell with one or more nucleic acid(s) encoding the protein, and allowing the expression of the nucleic acids by the host cell.

Preferred host cells are bacteria, like, for example, bacterial strain BL21 or strain SE1, or mammalian host cells, more preferably human host cells. Suitable mammalian host cells include human embryonic kidney (HEK-293) cells, PER.C6® cells or Chinese hamster ovary (CHO) cells, which can be commercially obtained. Insect cells, such as S2 or S9 cells, may also be used using baculovirus or insect cell expression vectors, although they are less suitable when the polypeptides according to the invention include elements that involve glycosylation. The single-chain polypeptides produced can be extracted or isolated from the host cell or, if they are secreted, from the culture medium of the host cell. Thus, in one embodiment, a method comprises providing a host cell with one or more nucleic acid(s) encoding the polypeptides, allowing the expression of the nucleic acids by the host cell. It is included that the molecules are capable of specifically and effectively binding to an MHC-p complex and subsequently inducing apoptosis after engulfment of the bound molecules by the targeted aberrant cell. Methods for the recombinant expression of (mammalian) proteins in a (mammalian) host cell are well known in the art.

As will be clear, a molecule hereof finds its use in many therapeutic applications and non-therapeutic applications, e.g., diagnostics or scientific applications. Provided herein is a method for inducing ex vivo or in vivo apoptosis of a target cell, comprising contacting the cell with a polypeptide according to the invention in an amount that is effective to induce apoptosis. The target cells can be conveniently contacted with the culture medium of a host cell that is used for the recombinant production of the polypeptide. In one embodiment, it can be used for in vitro apoptosis studies, for instance, studies directed at the elucidation of molecular pathways involved in MHC class I- and class II-induced apoptosis. Molecules hereof may also be used for the detection of (circulating) tumor cells.

Preferably, the single-chain molecule is used for triggering apoptosis of aberrant cells in a subject, more preferably a human subject. For therapeutic applications in humans, it is, of course, preferred that a single-chain molecule does not contain amino-acid sequences of non-mammalian origin. More preferred are single-chain proteins, which only contain human amino-acid sequences apart from, e.g., apoptin, or which contain human amino-acid sequences including a minimal number of camelid-derived amino-acid residues. Therefore, a therapeutically effective amount of a polypeptide binding to a disease-specific epitope can be administered to a patient to stimulate specific apoptosis of aberrant cells without affecting the viability of (normal) cells not expressing the disease-specific epitope. It is demonstrated herein that a method of the invention allows for the killing of cells in an antigen-specific, MHC-restricted fashion. In a specific embodiment, the disease-specific epitope is a cancer-specific epitope, for example, a melanoma-specific epitope. The killing of aberrant cells, while minimizing or even totally avoiding the death of normal cells, will generally improve the therapeutic outcome of a patient following administration of the single-chain polypeptides according to the invention.

Accordingly, there is also provided a polypeptide according to the invention as a medicament. In another aspect, provided is the use of a polypeptide for the manufacture of a medicament for the treatment of cancer, autoimmune disease or any other disease of which the symptoms are reduced upon killing the cells expressing a disease-specific antigenic peptide or epitope in the context of MHC. For example, a polypeptide according to the invention is advantageously used for the manufacture of a medicament for the treatment of melanoma.

Antibody fragments of human origin can be isolated from large antibody repertoires displayed by phages. One aspect of the invention is the use of human antibody phage display libraries for the selection of human Fab or human VhCh fragments specific for MHC class I molecules presenting cancer testis antigenic peptides. Antibody fragments specific for MHC class I, i.e., HLA-A0201 molecules presenting a multi-MAGE-A epitope, have been selected (essentially as described in R. A. Willemsen et al., Cytometry A, 2008, 73:1093-1099) and shown to bind the relevant antigen only. As these antibody Fab fragments usually display low affinity, a method is provided that allows the generation of high avidity antibody chains able to induce apoptosis in a MHC-restricted antigenic peptide-specific way. An aspect of the present invention is the development of a single-chain polypeptide comprising multiple (up to four) antigen binding domains to enhance MHC-p complex binding avidity. Enhancing MHC-p complex binding avidity results in efficient cross-linking of the MHC-p complexes and engulfment of the MHC-p complexes with bound single-chain polypeptides according to the invention, subsequently followed by apoptin-mediated induction of apoptosis.

Throughout the specification, the term fragment refers to an amino-acid sequence that is part of a protein domain or that builds up an intact protein domain. Fragments according to the invention must have binding specificity for the respective target.

An MHC-p complex-specific polypeptide in a monovalent or multivalent single-chain polypeptide form of the invention is, for example, an MHC-restricted antigen-specific TCR-like antibody (Ab) or functional fragment thereof, which is used as a monomer or which is multimerized at the DNA level in order to obtain a single-chain polypeptide construct upon expression.

Antibody Fab fragments are composed of antibody variable domains, responsible for antigen binding, and parts of the constant domains, lacking immunologic function. The variable domains in antibody Fab fragments, the variable heavy ($V_H$) and variable light ($V_L$) chain domains both bind the antigen. However, in many circumstances, the $V_H$ chain alone is able and sufficient to bind antigen, for example, in VhCh fragments. As such, antibody $V_H$ domains would provide small functional binding units.

Human $V_H$ domains usually do not meet the standards for stability and efficient expression that are required by the field, especially when derived from Fab and ScFv libraries. They tend to be unstable and poorly expressed. A process called "camelization" may be used to convert human $V_H$ into more stable antibody fragments.

The human antibody germline region $V_H$-3 displays high homology with antibody $V_H$ fragments of llamas. Llamas have two types of antibodies, those composed of heavy and light chains, and antibodies that only contain heavy chains. These heavy-chain only antibodies bind antigens similar to classical antibodies composed of heavy and light chains. The smallest functional llama antibody binding domain, the $V_{HH}$ domain, also called single domain antibodies (sdAb), have been shown to be expressed well and may bind antigen with high affinity. In addition, it has been shown that some of the characteristics, such as ease of expression and stability, of llama sdAb can be transferred to, e.g., human $V_H$ by replacing a few amino acids in the human $V_H$ for those of llama $V_H$. High avidity antibody molecules can then be generated by ligation of several "camelized" human VH domains into one single molecule.

Figure 5:
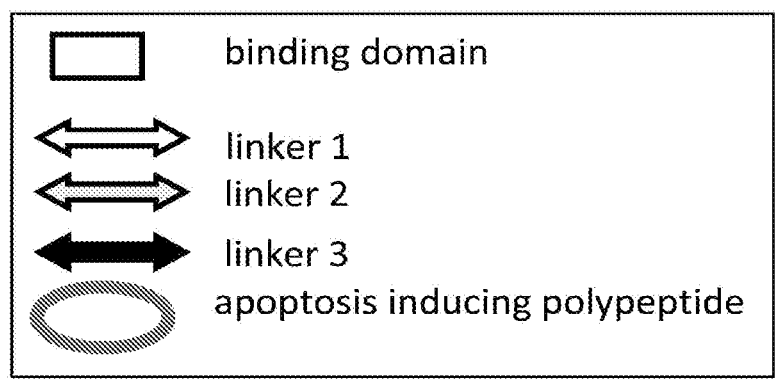
FIG. 5: Cartoon displaying examples of preferred binding molecules. Examples are provided of possible numbers of VH domains and distinct linker sequences for the construction of multi-domain proteins. In rows a and c, two examples are provided of proteinaceous molecules of the invention, comprising one or two binding domains, with the apoptosis-inducing polypeptide or protein linked at the C-terminal site of the binding domain. In rows b and d-f, the exemplified preferred proteinaceous molecules of the invention comprise one, two, three or four consecutive binding domains, linked through different linkers between consecutive domains, with the apoptosis-inducing polypeptide or protein linked at the N-terminal site of the N-terminal binding domain.
Figure 5:
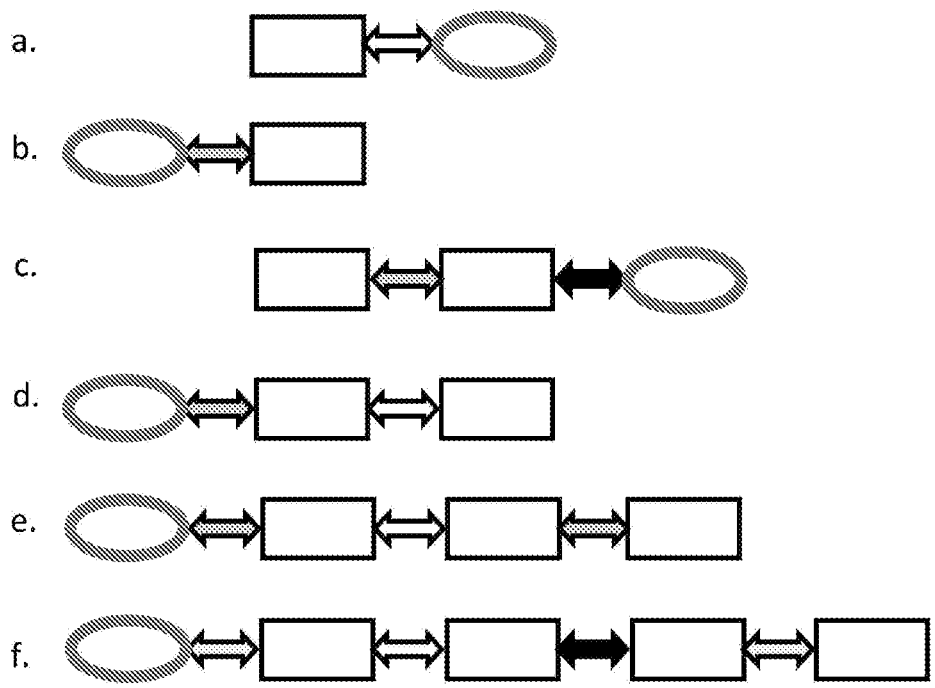

Preferred molecules comprise 1-6 "camelized" or "non-camelized" human VH domains interspersed by short linkers providing flexibility between the VH domains and between the binding domains and apoptin. For example, a tetravalent protein is generated that is specific for the HLA-A0201 restricted multi-MAGE-A epitope as part of a single-chain polypeptide comprising the apoptin polypeptide. These proteins according to the invention are referred to as a single-chain protein or (single-chain) polypeptide or monomeric protein or monomeric polypeptide. See, for further details, the outlined Examples below. It is to be appreciated that this technology allows for the generation of multivalent single-chain proteins that comprise any number of the same or different binding domains such as single domain antibodies or human VH domains. For several reasons (such as ease of production), repeats are not always the best option. Thus, the invention also contemplates using different binding domains (essentially recognizing the same target) separated by several different linkers, as shown in FIG. 5.

For example, a tetravalent single-chain polypeptide according to the invention, consisting of four linked camelized or non-camelized human VH domains connected through peptide bonds to apoptin, is used, for example, to induce apoptosis in cancer cells that express both the MAGE-A genes and HA-A0201. Noteworthy, specificity for this MHC-p complex is provided in this way as cells that do not express HLA-A0201 or that do not express MAGE-A are not killed. See the Examples section for further details.

Apoptosis in cancer cells is, for example, detected in vitro by several assays known to the art, including cytotoxicity assays, tunnel assays and assays detecting active caspases. In animal studies, apoptosis is, for example, revealed by monitoring reduced tumor growth, detection of active caspases or performing a tunnel assay on isolated tumor material.

In literature, it is shown that a single nine amino-acid (A.A.) peptide present in MAGE-A2, -A3, -A4, -A6, -A10, and -A12 is presented by HLA-A0201 on tumor cells, and can be recognized by cytotoxic T lymphocytes.[1] This nine A.A. peptide with sequence Y-L-E-Y-R-Q-V-P-G (SEQ ID NO:11) is almost identical to the HLA-A0201 presented MAGE-A1 peptide Y-L-E-Y-R-Q-V-P-D (SEQ ID NO:22), except for the anchor residue at position 9. Replacement of the anchor residue with Valine results in a 9 A.A. peptide with enhanced binding capacity to HLA-A0201 molecules. $^{(1)}$ Human and mouse T lymphocytes recognizing the Y-L-E-Y-R-Q-V-P-V (SEQ ID NO:23) peptide presented by HLA-0201 also recognize the original MAGE-A Y-L-E-Y-R-Q-V-P-G (SEQ ID NO:11) and Y-L-E-Y-R-Q-V-P-D (SEQ ID NO:22) peptides presented on tumors of distinct origin. As diverse tumors may each express at least one MAGE-A gene, targeting of this so-called multi-MAGE-A epitope includes the vast majority of tumors. As an example, MAGE-A expression in human prostate tumor cell lines and in human xenographs was analyzed and shown to be highly diverse, but in each individual sample tested, at least one MAGE-A gene was expressed (Table 2), continuing that targeting this multi-MAGE-A epitope serves as a universal HLA-A0201-restricted target for therapy. Of course, several other multi-MAGE-A or multi-target epitopes may be discovered. In principle, the invention contemplates combinations of tumor-specific antigen-derived MHC-presented epitopes in different HLA restrictions of both MHC-I and MHC-II targeted by monomeric or multimeric (preferably, n=2-4) binding domains linked to an apoptosis-inducing polypeptide or protein, to induce apoptosis in aberrant cells. A number of MHC-MAGE peptide combinations that can be targeted are IMPKAGLLI (MAGE-A3) (SEQ ID NO:21), and HLA-DP4 or HLA-DQ6/243-KKLLTQHFVQENY-LEY-258 (MAGE-A3) (SEQ ID NO:24). Other examples of tumor-specific complexes of HLA and antigen peptide are (N. Renkvist et al., Cancer Immunol. Immunother. (2001) V50:3-15): HLA A1-MAGE-A1 peptide EADPTGHSY (SEQ ID NO:25), HLA A3-MAGE-A1 SLFRAVITK (SEQ ID NO:26), HLA A24-MAGE-A1 NYKHCFPEI (SEQ ID NO:27), HLA A28-MAGE-A1 EVYDGREHSA (SEQ ID NO:28), HLA B37-MAGE-A1/A2/A3/A6 REPVTKAEML (SEQ ID NO:29), expressed at aberrant cells related to melanoma, breast carcinoma, SCLC, sarcoma, NSCLC, colon carcinoma. Further examples are HLA B53-MAGE-A1 DPARYEFLW (SEQ ID NO:30), HLA Cw2-MAGE-A1 SAFPTTINF (SEQ ID NO:31), HLA Cw3-MAGE-A1 and HLA Cw16-MAGE-A1 SAYGEPRKL (SEQ ID NO:32), HLA A2-MAGE A2 KMVELVHFL (SEQ ID NO:33), HLA A2-MAGE-A2 YLQLVFGIEV (SEQ ID NO:34), HLA A24-MAGE-A2 EYLQLVFGI (SEQ ID NO:35), HLA-A1-MAGE-A3 EADPIGHLY (SEQ ID NO:36), HLA A2-MAGE-A3 FLWGPRALV (SEQ ID NO:37), HLA B44-MAGE-A3 MEVDPIGHLY (SEQ ID NO:38), HLA B52-MAGE-A3 WQYFFPVIF (SEQ ID NO:39), HLA A2-MAGE-A4 GVYDGREHTV (SEQ ID NO:40), HLA A34-MAGE-A6 MVKISGGPR (SEQ ID NO:41), HLA A2-MAGE-A10 GLYDGMEHL (SEQ ID NO:42), HLA Cw7-MAGE-A12 VRIGHLYIL (SEQ ID NO:43), HLA Cw16-BAGE AARAVFLAL (SEQ ID NO:44), expressed by, for example, melanoma, bladder carcinoma, NSCLC, sarcoma, HLA A2-DAM-6/-10 FLWGPRAYA (SEQ ID NO:45), expressed by, for example, skin tumors, lung carcinoma, ovarian carcinoma, mammary carcinoma, HLA Cw6-GAGE-1/-2/-8 YRPRPRRY (SEQ ID NO:46), HLA A29-GAGE-3/-4/-5/-6/-7B YYWPRPRRY (SEQ ID NO:47), both expressed by, for example, melanoma, leukemia cells, bladder carcinoma, HLA B13-NA88-A MTQGGQHFLQKV (SEQ ID NO:48), expressed by melanoma, HLA A2-NY-ESO-1 SLLMWITQCFL (SEQ ID NO:49), HLA A2-NY-ESO-1a SLLMWITQC (SEQ ID NO:50), HLA A2-NY-ESO-1a Art (SEQ ID NO:51), HLA A31-NY-ESO-1a ASGPGGGAPR (SEQ ID NO:52), the latter four expressed by, for example, melanoma, sarcoma, B lymphomas, prostate carcinoma, ovarian carcinoma, bladder carcinoma.

In one embodiment, human antibody fragments specific for the HLA-A0201-presented multi-MAGE-A epitope Y-L-E-Y-R-Q-V-P-V (SEQ ID NO:23) are identified and isolated from a human Fab phage display library. The selected human antibody fragments are optimized regarding their specificity and avidity, and provide the amino-acid sequences used for the design and production of monovalent, divalent, trivalent, tetravalent, mono-specific single-chain polypeptides comprising apoptin and specific for efficient binding of the HLA-A0201-MAGE-A epitope Y-L-E-Y-R-Q-V-P-G (SEQ ID NO:11), referred to as mono-AH5-apoptin, di-AH5-apoptin, tri-AH5-apoptin, tetra-AH5-apoptin. In another embodiment, mono-AH5-apoptin, di-AH5-apoptin, tri-AH5-apoptin, tetra-AH5-apoptin, is produced comprising a cathepsin-L or cathepsin-B cleavage amino-acid sequence, providing mono-AH5-Cath-apoptin, di-AH5-cath-apoptin, tri-AH5-cath-apoptin, tetra-AH5-cath-apoptin, with essentially the same or comparable binding characteristics compared to mono-AH5-apoptin, di-AH5-apoptin, tri-AH5-apoptin, tetra-AH5-apoptin.

In one embodiment, for example, the mono-AH5-apoptin, di-AH5-apoptin, tri-AH5-apoptin, tetra-AH5-apoptin, and/or its equivalents mono-AH5-Cath-apoptin, di-AH5-cath-apoptin, tri-AH5-cath-apoptin, tetra-AH5-cath-apoptin are used in the production of a pharmaceutical composition. In yet another embodiment, monovalent or multivalent AH5-apoptin construct is used for the production of a pharmaceutical composition for the treatment of a disease or a health problem related to the presence of aberrant cells exposing the epitope comprising the HLA-A0201-MAGE-A epitope Y-L-E-Y-R-Q-V-P-G (SEQ ID NO:11) complex for monovalent or multivalent AH5-apoptin, monovalent or multivalent AH5-cath apoptin. The aberrant cells are, for example, tumor cells. In a further embodiment, monovalent or multivalent AH5-apoptin and/or its equivalents monovalent or multivalent AH5-cath-apoptin is used for the treatment of cancer. In yet another embodiment, monovalent or multivalent AH5-apoptin and/or its equivalents is used, for example, for the treatment of prostate cancer, breast cancer, multiple myelomas or melanomas.

The invention is exemplified by the Examples below.

ABBREVIATIONS USED

A.A., amino acid; Ab, antibody; ADA, anti-drug antibodies; AFP, alpha-fetoprotein; APC, antigen-presenting cell; β2-M, β2-microglobulin; CAV, chicken anemia virus; CD, circular dichroism; CDR, complementarity-determining region; CEA, carcino-embryonic antigen; CHO, Chinese hamster ovary; CKIIα, catalytic subunit of casein kinase II; CT, cancer testis antigens; CTL, cytotoxic T lymphocyte; DC, dendritic cell; E4orf4, adenovirus early region 4 open reading frame; EBV, Epstein-Barr virus; ELISA, enzyme linked immunosorbent assay; HAMLET, human α-lactalbumin made lethal to tumor cells; HEK, human embryonic kidney; HLA, human leukocyte antigen; Ig, immunoglobulin; i.v., intravenously; kDa, kilo Dalton; MAGE, melanoma-associated antigen; Mda-7, melanoma differentiation-associated gene-7; MHC, major histocompatibility complex; MHC-p, MHC-peptide; MVM, parvovirus minute virus of mice; NS1, parvovirus-H1-derived non-structural protein 1; PBSM, PBS containing 2% non-fat dry milk; PTD4, protein transduction domain 4; sc-Fv, single-chain variable fragment; $V_{HH}$ or sdAb, single-domain antibodies; TCR, T-cell receptor; VH, Vh or $V_H$, variable amino-acid sequence of an antibody heavy domain; TRAIL, tumor necrosis factor-related apoptosis-inducing ligand.

EXAMPLES

Example 1: Selection of Human Antibody Fragments Specific for HLA-A0201/Multi-MAGE-A To obtain human antibody fragments specific for the HLA-A0201-presented multi-MAGE-A epitope Y-L-E-Y-R-Q-V-P-G (SEQ ID NO:11) or Y-L-E-Y-R-Q-V-P-V (SEQ ID NO:23), a Human Fab phage display library was constructed according to the procedure previously described by de Haard et al.[(2)] and used for selections essentially as described by Chames et al.[(3)] Alternatively, a human VhCh library was constructed and used for selections. Human Fab/VhCh phages ($10^{13}$ colony-forming units) were first pre-incubated for 1 hour at room temperature in PBS containing 2% non-fat dry milk (PBSM). In parallel, 200 μl Streptavidin-coated beads (Dynal™) were equilibrated for 1 hour in PBSM. For subsequent rounds, 100 μl beads were used. To deplete for pan-MHC binders, each selection round, 200 nM of biotinylated MHC class I-peptide (MHC-p) complexes containing an irrelevant peptide (Sanquin, the Netherlands) were added to the phages and incubated for 30 minutes under rotation. Equilibrated beads were added, and the mixture was incubated for 15 minutes under rotation. Beads were drawn to the side of the tube using magnetic force. To the depleted phage fraction, subsequently decreasing amounts of biotinylated MHC-p complexes (200 nM for the first round, and 20 nM for the second and third rounds) were added and incubated for 1 hour at room temperature, with continuous rotation. Simultaneously, a pan-MHC class I binding-soluble Fab (D3) was added to the phage-MHC-p complex mixture (50, 10, and 5 μg for rounds 1-3, respectively). Equilibrated streptavidin-coated beads were added, and the mixture was incubated for 15 minutes under rotation. Phages were selected by magnetic force. Non-bound phages were removed by five washing steps with PBSM, five steps with PBS containing 0.1% TWEEN®, and five steps with PBS. Phages were eluted from the beads by 10 minutes incubation with 500 μl freshly prepared tri-ethylamine (100 mM). The pH of the solution was neutralized by the addition of 500 μl 1 M Tris (pH 7.5). The eluted phages were incubated with logarithmic growing E. Coli TG1 cells ($OD_{600nm}$ of 0.5) for 30 minutes at 37° C. Bacteria were grown overnight on 2×TYAG plates. Next day, colonies were harvested, and a 10 μl inoculum was used in 50 ml 2×TYAG. Cells were grown until an $OD_{600nm}$ of 0.5, and 5 ml of this suspension was infected with M13k07 helper phage ($5 \times 10^{11}$ colony-forming units). After 30 minutes incubation at 37° C., the cells were centrifuged, resuspended in 25 ml 2×TYAK, and grown overnight at 30° C. Phages were collected from the culture supernatant as described previously, and were used for the next round panning. After three selection rounds, a 261-fold enrichment of Fab phages was obtained, and 46 out of 282 analyzed clones were shown to be specific for the HLA-A2-multi-MAGE-A complex (FIG. 1). ELISA using the HLA-A0201/multi-MAGE-A complexes as well as HLA-A0201 complexes with a peptide derived from JC virus was used to determine the specificity of the selected Fab.

Figure 2:
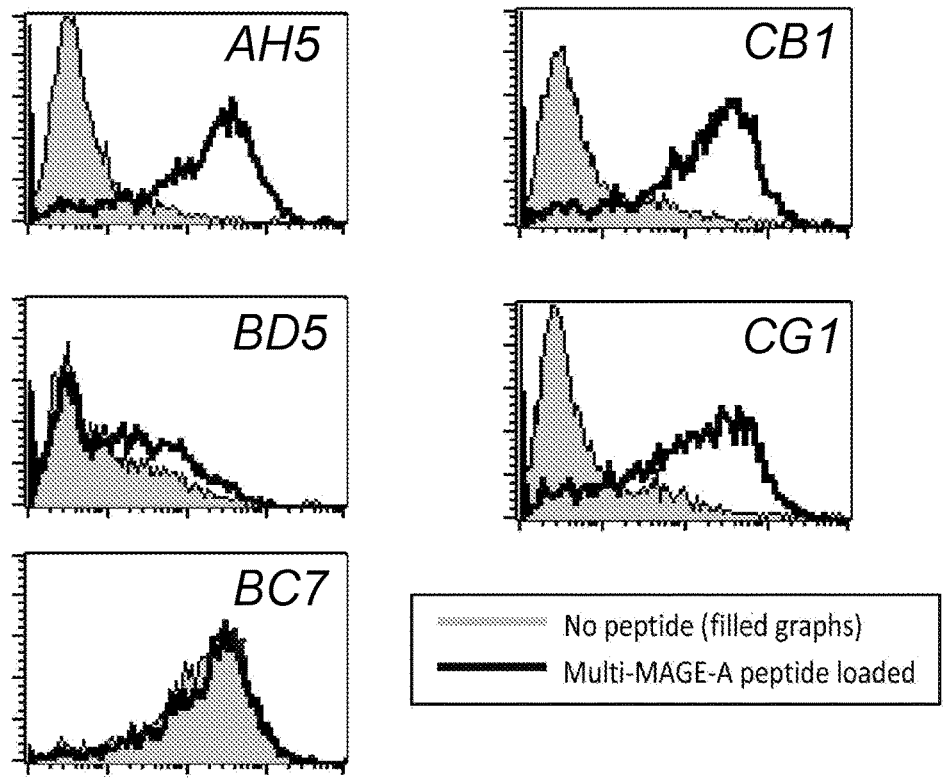
FIG. 2: Phages AH5, CB1 and CG1 specifically bind cells presenting the multi-MAGE-A peptide. Phages AH5, CB1, CG1, BD5 and BC7 that had shown specific binding in ELISA using the relevant HLA-A201/multi-MAGE-A complex and an irrelevant HLA-A201 complex loaded with a JCV peptide were analyzed for their capacity to bind cells presenting the multi-MAGE-A peptide in HLA-A0201 molecules. To this end, human B-LCL (BSM) were loaded with multi-MAGE-A peptide (10 µg in 100 µl PBS) for 30 minutes at 37° C., followed by incubation with the Fab phages AH5, CB1, CG1, BD5 and BC7 and analyzed by flow-cytometry using anti-phage antibodies and a fluorescently labeled secondary antibody.

Human Fab Specific for the HLA-A0201/Multi-MAGE-A Epitope Bind Antigen-Positive Cells Selected Fab phages were then analyzed for their capacity to bind HLA-A0201-positive EBV-transformed B-LCL loaded with the multi-MAGE-A peptide Y-L-E-Y-R-Q-V-P-V (SEQ ID NO:23). The B-LCL line BSM ($0.5 \times 10^6$) was loaded with multi-MAGE-A peptide (10 μg in 100 μl PBS) for 30 minutes at 37° C., followed by incubation with the Fab phages AH5, CB1, CG1, BD5 and BC7 and analyzed by flow-cytometry. As shown in FIG. 2, Fab AH5, CB1 and CG1 specifically bound to the peptide-loaded cells only, whereas Fab BD5 and BC7 displayed non-specific binding to BSM that was not loaded with the multi-MAGE-A peptide. No binding was observed by AH5, CB1 and CG1 non-peptide-loaded cells.

Figure 3:
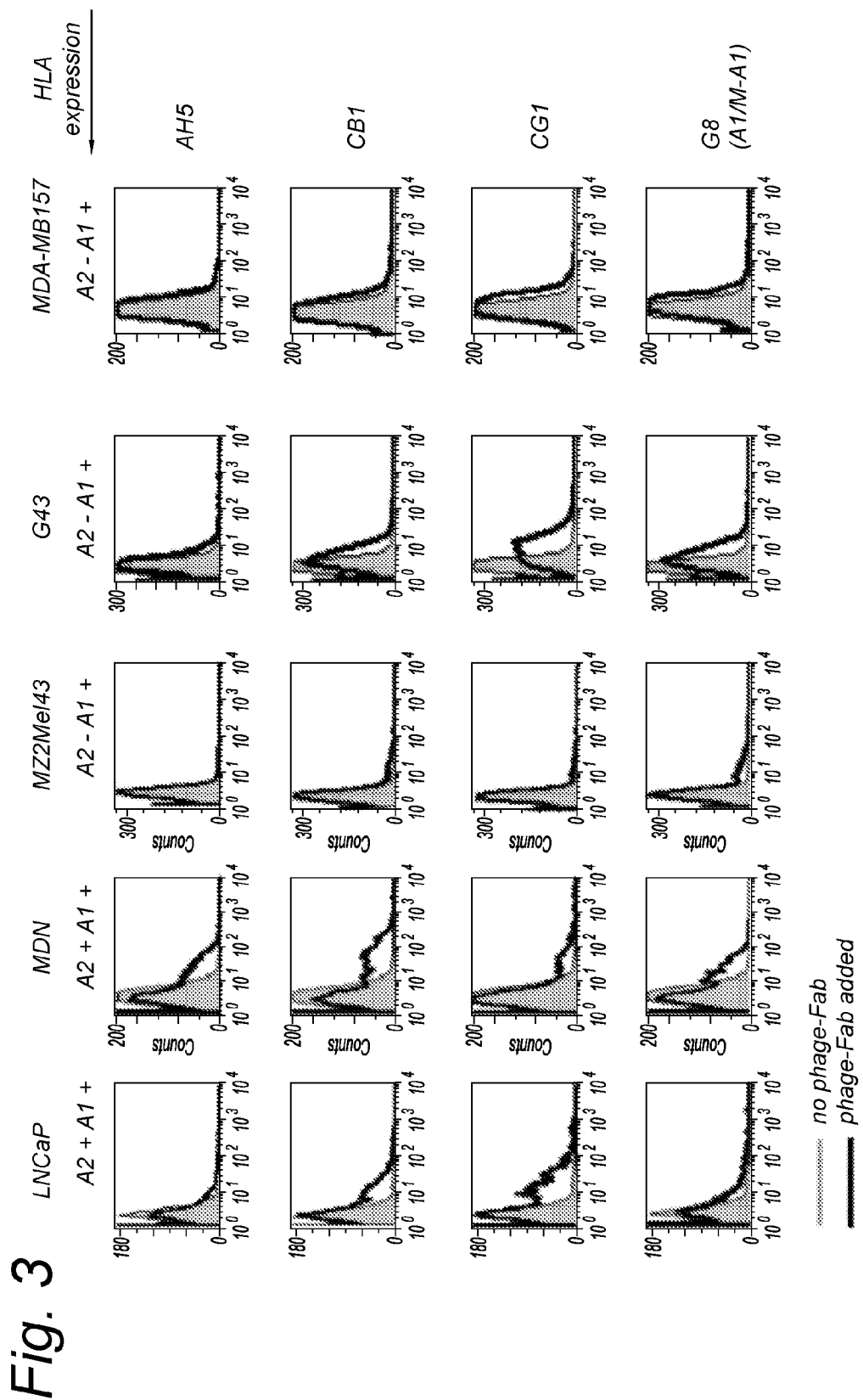
FIG. 3: Phages expressing HLA-A2/multi-MAGE-A specific Fab bind tumor cells of distinct histologic origin. Phages AH5, CB1 and CG1 specific for HLA-A0201/multi-MAGE-A and a positive control phage specific for HA-0101/MAGE-A1 were used for staining of distinct tumor cell lines. To this end, the prostate cancer cell line LNCaP, the multiple myeloma cell line MDN, the melanoma cell lines MZ2-MEL43 and G43, and the breast cancer cell line MDA-MD157 were incubated with the different phages (30 minutes at 4° C.); bound phages were then detected by flow cytometry using anti-phage antibodies and fluorescently labeled secondary antibodies.

Phages presenting AH5, CB1 and CG1, as well as the HLA-A0101/MAGE-A1-specific Fab phage G8[(4)] were then used to stain tumor cell lines of distinct histologic origin. To this end, prostate cancer cells (LNCaP), multiple myeloma cells (MDN), melanoma cells (MZ2-MEL43 and G43), and breast cancer cells (MDA-MB157) were stained and analyzed by flow cytometry (FIG. 3). The Fab AH5 specifically bound multiple myeloma cells MDN, and not the HLA-A0201-negative melanoma and breast cancer cells. Both CB1 and CG1 displayed non-specific binding on the melanoma cell line G43. The positive control Fab G8 demonstrated binding to all cell lines tested.

Fab AH5 Binds HLA-A0201/Multi-MAGE-A Complexes Only

Figure 4:
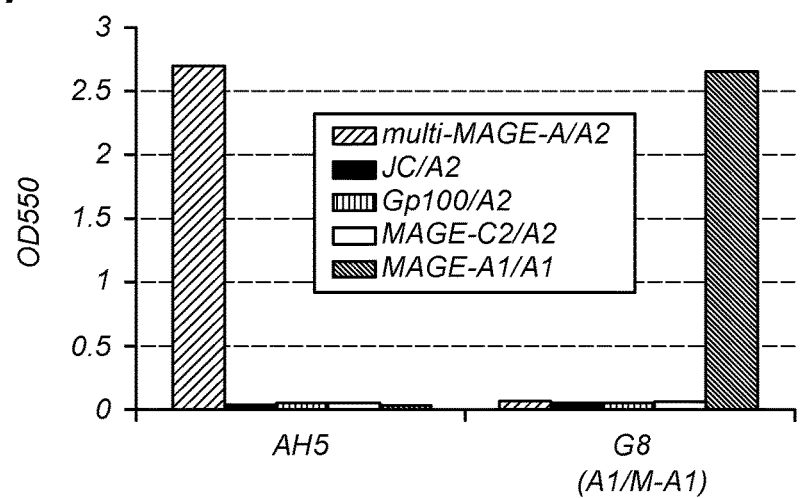
FIG. 4: Phage AH5 specifically binds HLA-A0201/multiMAGE-A complexes only. To determine specificity of the phage AH5, an ELISA was performed using relevant and irrelevant peptide/MHC complexes. HLA-A0201 with multi-MAGE-A, gp100, JCV and MAGE-C2 peptides, as well as HLA-A1 with MAGE-A1 peptide, were coated on streptavidin 96-well plates and incubated with phage AH5.

ELISA using multiple peptide/MHC complexes then confirmed the specificity of Fab-AH5. To this end, HLA-A0201 complexes-presenting peptides multi-MAGE-A, gp100, JCV and MAGE-C2, as well as a HLA-A1/MAGE-A1 complex, were immobilized on 96-well plates and incubated with phages displaying Fab AH5 and control Fab G8. As shown in FIG. 4, AH5 only binds HLA-A0201/multi-MAGE-A and not the irrelevant complexes HLA-A0201/gp100, HLA-A0201/MAGE-C2, HLA-A0201/JCV and HLA-A0101/MAGE-A1. The positive control Fab G8 only binds to its relevant target HLA-A0101/MAGE-A1.

Example 2: Production of Monovalent and Multivalent AH5-Apoptin Polypeptides and Monovalent and Multivalent AH5-Cath-Apoptin Polypeptides Design of Genes for Production of Tetrameric AH5 VH-Apoptin and AH5 Vh-Cath-Apoptin Human antibody germline gene VH3 demonstrates high homology to llama single domains VHH. Exchange of amino-acids 44, 45 and 47 in the human VH3 genes by amino-acids present in llama VHH at these positions has shown to enhance stability and expression of the human VH3 genes. All substitutions described to have an effect on protein stability and/or solubility include: E6A, A33C, V37F, G44E, L45R, W47G, S74A, R83K, A84P or L108Q.

Figure 6:
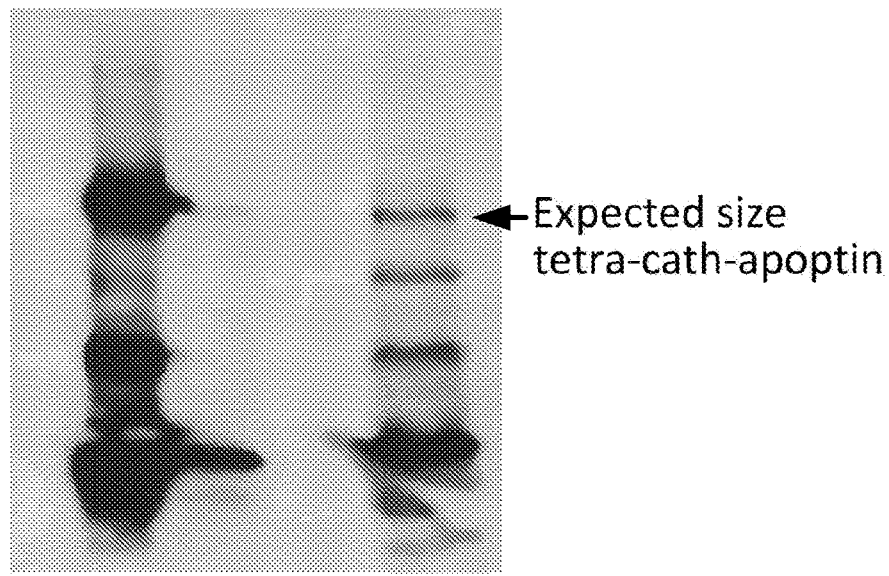
FIG. 6: The antibody-apoptin fusion protein is produced in SE-1 bacteria. The pStaby 1.2 tetra-AH5-apoptin (SEQ ID NO:21, amino-acid sequence (Vh)4-cath-apoptin) construct was introduced into SE-1 Bacteria and grown to OD=0.6 at 30° C. Protein production was induced by addition of IPTG to a final concentration of 1 mM and bacteria were grown at 30° C. for 13 hours. Lane 1: total fraction of bacteria producing the antibody-apoptin fusion protein; lane 2: periplasmic fraction of bacteria; lane 3: flow-through of affinity purified antibody-apoptin fusion protein; lane 4: eluted fraction of antibody-apoptin protein.
Figure 7:
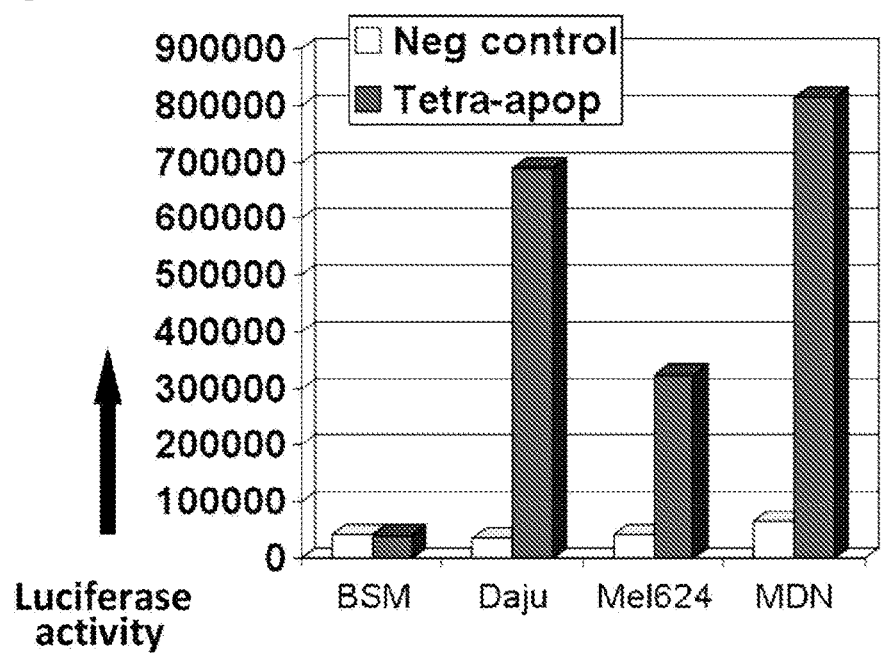
FIG. 7: The antibody-apoptin fusion protein induces apoptosis in cancer cells. Purified antibody-apoptin fusion protein was incubated for 6 hours with HLA-A0201-positive cell lines expressing MAGE-A genes (Daju, Mel624 and MDN) and a HLA-A0201-positive, MAGE-A-negative EBV-transformed B-cell line (BSM). As a negative control, a periplasmic fraction of non-induced SE-1 bacteria was used. After incubation, caspase-3 activity was measured by "Caspa-Glow" assay (according to the manufacturer's instructions, Promega). As shown, only HLA-A0201/MAGE-A-positive cells show active caspase-3 activity. MAGE-A-negative cells and cells incubated with the negative control protein fraction do not show any signs of apoptosis.

The AH5 VH demonstrates a low homology to germline gene VH3-33*01 (71% as determined by IMGT homology search); however, its expression and stability might benefit from the exchange of amino-acids 6, 44, 45 and 47 and 108 by llama VHH amino-acid residues, a process called camelization. In addition, a gene was compiled that upon expression, comprises four AH5 VH domains. To this end, a gene called tetra-AH5 was designed comprising the pelB secretion signal, four codon-optimized, camelized AH5 VH domains with Gly-Ser linkers between each AH5 VH domain, and finally the apoptin gene (see tetra-AH5-apoptin, see SEQ ID NO:16 for the amino-acid sequence). The Tetra AH5-cath-apoptin gene comprises the pelB secretion signal, four codon-optimized, camelized AH5 VH domains with Gly-Ser linkers between each AH5 VH domain, the cathepsin-L cleavage site and finally the apoptin gene (see tetra-AH5-cath-apoptin, see SEQ ID NO:21 for the amino-acid sequence). This gene was synthesized by "Geneart" (Regensburg, Germany) and cloned into the pStaby 1.2 vector (Delphi Genetics, Belgium) for expression in *E. coli*.
Production and Purification of Tetrameric AH5 VH-Apoptin Protein For expression of tetra-AH5-cath-apoptin, the pStaby-tetra-AH5-cath-apoptin vector was introduced via electroporation into SE1 bacteria. Positive clones were grown in the presence of 2% glucose at 30° C. until $OD_{600}$=0.8. Bacterial TYAG medium was then replaced with TY medium containing 1 mM IPTG to induce expression. After 4 hours or overnight culture at 30° C., bacteria and medium were harvested. The periplasmic fraction was collected after incubation of bacteria with PBS/EDTA/NaCl for 30 minutes on ice. Protein expression was analyzed by SDS-PAGE. It is shown that tetra-cath-apoptin protein is secreted into the bacterial periplasm and medium (see FIG. 6).

Tetra-AH5-cath-apoptin was isolated from media and bacterial periplasm using Ni-affinity purification. To this end, desalted periplasmic fractions were purified on Acta-FPLC with His-trap column or alternatively incubated with Ni-coupled Sepharose-beads and incubated overnight while stirring gently at 4° C. To obtain intracellular proteins, bacteria was lysed and cellular debris removed by centrifugation. After overnight dialysis with PBS, tetrameric AH5 VH-apoptin and tetrameric AH5-cath-apoptin was purified with Ni-Sepharose. Purity of the proteins were checked by SDS-PAGE and protein concentration determined by BCA protein assay (Pierce).

Example 3: Cell Binding and Internalization of Tetra-AH5-Cath-Apoptin

Binding capacity of tetra-AH5-cath-apoptin was analyzed by flow-cytometry. HLA-A0201/multi-MAGE-A-positive tumor cells (Daju, MDN and mel 624) and HLA-A0201/multi-MAGE-A-negative cells (BSM, G43 and 293) were incubated on ice with purified protein and detected by addition of fluorescently labeled anti-His antibodies. Cells bound by the proteins were quantified and visualized by flow cytometry. Internalization of tetra-AH5-cath-apoptin was analyzed by confocal microscopy. To this end, cells were incubated with the proteins, kept on ice for 30 minutes to allow binding but no internalization. Next, fluorescently labeled anti-His antibodies were added. To induce internalization, cells were transferred to 37° C. and fixed with 1% PFA after 5, 10 and 15 minutes.

Example 4: Apoptosis Induction by Tetra AH5-Cath-Apoptin in Diverse Tumor Cells

Killing of Diverse Tumor Cells by Tetra-AH5-Cath-Apoptin
Tetra-AH5-cath-apoptin was analyzed for its capacity to induce apoptosis by incubation with diverse tumor cells, known to express both HLA-A0201 and MAGE-A genes. The cell lines Daju, Mel 624 (melanoma), PC346C (prostate cancer), and MDN (multiple myeloma), as well as MAGE-A-negative cells (BSM, and 911, HEK293T), were incubated with different concentrations of the proteins (in DMEM medium, supplemented with pen/strep, Glutamine and non-essential amino acids). Several hours later, cells were visually inspected for classical signs of apoptosis such as detachment of the cells from tissue culture plates and membrane blebbing. It is excepted that the proteins induce apoptosis in the Daju Mel 624, PC346C and MDN cells. Cells that are not treated with the proteins will not be affected, as well as cells that do not express HLA-A0201 (HEK293T) and MAGE-A genes (911 and HEK293T).
Detection of Active Caspase-3
A Classical Intra-Cellular Hallmark for Apoptosis is the Presence of Active Caspase-3.

To determine whether or not tetra-AH5-cath-apoptin induces active caspase-3, HLA-A0201/MAGE-A-positive cells (Daju, Mel624 and MDN), as well as HLA-A0201-positive, but not MAGE-A-negative cells (BSM), were incubated with tetra-AH5-cath-apoptin. After four and 13 hours, FAM-DEVD-FMK, a fluorescently caspase-3/7 inhibitor, was added and positively stained cells visualized by fluorescent microscopy and flow cytometry. It was expected that caspase-3 activity was shown in antigen-positive cells and not in antigen-negative cells.

Treatment of tumor-bearing mice with tetra-AH5-apoptin and tetra-cath-apoptin
Nude mice (NOD-scid, eight per group) with a palpable subcutaneous transplantable human tumor (Daju or MDN) was injected with different doses of tetra-AH5-apoptin or tetra-AH5-cath-apoptin. As a control, mice were treated with standard chemotherapy or received an injection with PBS. It was expected that mice receiving an optimal dose of the proteins would survive significantly longer that those mice receiving chemotherapy or PBS.

TABLE 1

Examples of the frequency of MAGE-A expression by human cancers.
Frequency of expression (%)

| cancer | MAGE-A1 | MAGE-A2 | MAGE-A3 | MAGE-A4 | MAGE-A6 | MAGE-A10 | MAGE-A11 |
|---|---|---|---|---|---|---|---|
| Melanoma | 16 | E | 36 | E | 64 | E | 74 |
| Head and neck | 25 | 42 | 33 | 8 | N | N | N |
| Bladder | 21 | 30 | 35 | 33 | 15 | N | 9 |
| Breast | 6 | 19 | 10 | 13 | 5 | N | N |
| Colorectal | N | 5 | 5 | N | 5 | N | N |
| Lung | 21 | 30 | 46 | 11 | 8 | N | N |
| Gastric | 30 | 22 | 57 | N | N | N | N |
| Ovarian | 55 | 32 | 20 | E | 20 | N | N |
| osteosarcoma | 62 | 75 | 62 | 12 | 62 | N | N |
| hepatocarcinoma | 68 | 30 | 68 | N | 30 | 30 | 30 |

TABLE 1-continued

Examples of the frequency of MAGE-A expression by human cancers.

| | Frequency of expression (%) | | | | | | |
|---|---|---|---|---|---|---|---|
| cancer | MAGE-A1 | MAGE-A2 | MAGE-A3 | MAGE-A4 | MAGE-A6 | MAGE-A10 | MAGE-A11 |
| Renal cell carcinoma | 22 | 16 | 76 | 30 | N | N | N |

E, expressed but the frequency is not known;
N, expression by tumors has never been determined or observed

TABLE 1B

Expression analysis of MAGE-A1-A6 genes detected by nested RT-PCR with common primers in squamous cell carcinoma of the head and neck.

| Primary site | % of positive expression |
|---|---|
| Larynx | 72.7% (8/11) |
| Hypopharynx | 100% (2/2) |
| Base of tongue | 50% (1/2) |
| Tonsil | 100% (2/2) |
| Total (n = 17) | 76.5% (13/17) |

Adapted from: ANTICANCER RESEARCH 26: 1513-1518 (2006)

TABLE 2

MAGE-A expression in human prostate cancer cell lines and prostate cancer xenografts.

| Cell line/ Xenograft | MAGE- | | | | | | | | | | | |
|---|---|---|---|---|---|---|---|---|---|---|---|---|
| | A1 | A2 | A3 | A4 | A5 | A6 | A7 | A8 | A9 | A10 | A11 | A12 |
| LNCaP | + | ++ | ++ | | | ++ | + | | | | | |
| PC346C | + | ++ | ++ | + | | ++ | + | | | + | ++ | |
| OV-CAR | | + | + | | + | | + | | | | | |
| JON | | ++ | ++ | | ++ | | | | | + | + | |
| PNT 2 C2 | | + | + | | + | | | | | + | + | |
| SD48 | | | + | | + | | | | | + | + | |
| PC-3 | | | | | + | | | | | + | + | |
| PC 374 | | + | | | | | | | | | | |
| PC 346p | + | ++ | ++ | | ++ | | + | | | ++ | + | |
| PC 82 | | + | + | | | | | | | | | |
| PC 133 | ++ | + | | | | + | | | | | | |
| PC 135 | + | | | | | | | | | | | |
| PC 295 | + | | | | | | | | | | | |
| PC 324 | | + | | + | | + | | | | | | |
| PC 310 | + | ++ | | + | | ++ | | | | | + | |
| PC 339 | | ++ | ++ | | + | ++ | + | + | | | + | |

Expression of the MAGE-A1, A2, A3, A4, A5, A6, A7, A8, A9, A10, A11 and A12 genes in diverse prostate tumor cell lines and prostate xenografts was analyzed by RT-PCR. Shown are expression levels in individual samples tested. Blank = no expression, + = low expression, ++ = high expression.
All cell lines/xenografts express at least one MAGE-A gene.

REFERENCES

1. Stephanie Graff-Dubois, Olivier Faure, David-Alexandre Gross, Pedro Alves, Antonio Scardino, Salem Chouaib, Francois A. Lemonnier and Kostas Kosmatopoulos. Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy. *The Journal of Immunology*, 2002, 169:575-580.

2. Hans J. de Haard, Nicole van Neer, Anneke Reurs, Simon E. Hufton, Rob C. Roovers, Paula Henderikx, Adriaan P. de Brume, Jan-Willem Arends, and Hennie R. Hoogenboom. A Large Non-immunized Human Fab Fragment Phage Library That Permits Rapid Isolation and Kinetic Analysis of High Affinity Antibodies. *The Journal of Biological Chemistry*, 1999, 274:18218-18230.

3. Chames P., H. R. Hoogenboom, and P. Henderikx. Selection of antigens against biotinylated antigens. In Antibody phage display, methods and protocols, Edited by P. M. O'Brien and R. Aitken. *Methods in Molecular Biology* 2002, 178:147-159.

4. Patrick Chames, Simon E. Hufton, Pierre G. Coulie, Barbara Uchanska-Ziegler, Hennie R. Hoogenboom. Direct selection of a human antibody fragment directed against the tumor T-cell epitope HLA-A1-MAGE-A1 from a nonimmunized phage-Fab library. *PNAS*, 2000, 97:7969-7974.

5. Mathieu H. M. Noteborn, Proteins selectively killing tumor cells. *Eur. J. Pharmacol.*, 2009, 625:165-173.

Danen-Van Oorschot A. A. A. M., D. F. Fischer, J. M. Grimbergen, B. Klein, S.-M. Zhuang, J. H. F. Falkenburg, C. Backendorf, P. H. A. Quax, J. A. Van der Eb and M. H. M. Noteborn (1997). Apoptin induces apoptosis in human transformed and malignant cells but not in normal cells. *Proc. Nat'l Acad. Sci., USA* 94:5843-5847.

Li X., N. Jin, Z. Mi, H. Lian, L. Sun, X. Li, and H. Zheng (2006). Antitumor effects of a recombinant fowlpox virus expressing Apoptin in vivo and in vitro. *Int. J. Cancer* 119(12):2948-57.

Olijslagers S. J., Y. H. Zhang, C. Backendorf, M. H. Noteborn (2007). Additive cytotoxic effect of apoptin and chemotherapeutic agents paclitaxel and etoposide on human tumour cells. *Basic Clin. Pharmacol. Toxicol.* 100(2):127-31.

Pedersen A. E., S. Bregenholt, B. Johansen, S. Skov, M. H. Claesson. MHC-I-induced apoptosis in human B-lymphoma cells is dependent on protein tyrosine and serine/threonine kinases. *Exp. Cell. Res.* 1999, 251:128-34.

Cao Y., Y. Lan, J. Qian, Y. Zheng, S. Hong, H. Li, M. Wang, L. W. Kwak, D. Lin, J. Yang, and Q. Yi. Targeting cell surface β2-microglobulin by pentameric IgM antibodies. *Br. J. Haematol.* 2011, 154:111-121.

McCurdy D. K., L. Q. Tai, K. L. Imfeld, M. Schwartz, F. Zaldivar, and M. A. Berman. Expression of melanoma antigen gene by cells from inflamed joints in juvenile rheumatoid arthritis. *J. Rheumatol.* 2002, 29:2219-2224.

Marcar L., N. J. Maclaine, T. R. Hupp, and D. W. Meek. Mage-A cancer/testis antigens inhibit p53 function by blocking its interaction with chromatin. *Cancer Res.* 2010, 70:10362-10370.

Willemsen R. A., P. Chames, E. Schooten, J. W. Gratama, and R. Debets. Selection of human antibody fragments directed against tumor T-cell epitopes for adoptive T-cell therapy. *Cytometry A.* 2008, 73:1093-1099.

D. K. McCurdy et al., *J. Rheumatol.* 2002, 29:2219-2224

What is claimed is:

1. A single-chain polypeptide comprising at least one camelized Vh domain of an antibody functionally connected with apoptin or a fragment and/or derivative thereof, able to induce apoptosis in aberrant cells, but not normal cells,
   wherein the at least one camelized Vh domain of an antibody specifically binds an MHC1-MAGE peptide.

2. The single-chain polypeptide of claim 1, wherein the single-chain polypeptide comprises SEQ ID NO:2.

3. A single polypeptide chain comprising:
   at least one domain comprising SEQ ID NO:2, wherein the domain specifically binds to an MHC1-MAGE peptide complex and wherein the at least one domain comprising SEQ ID NO:2 is linked via peptide bond with apoptin or a fragment and/or derivative thereof that upon administration to a cell induces apoptosis in an aberrant cell, but not in a normal cell.

4. A single-chain polypeptide comprising four camelized Vh domains of an antibody functionally connected with apoptin or a fragment and/or derivative thereof, able to induce apoptosis in aberrant cells, but not normal cells, wherein each of the four camelized Vh domains of an antibody specifically binds an MHC-1-MAGE peptide complex.

5. The single-chain polypeptide of claim 4, wherein the four camelized Vh domains of an antibody are selected from the group consisting of a domain comprising SEQ ID NO:2 and a domain comprising SEQ ID NO:13.

6. The single-chain polypeptide of claim 4, wherein the four camelized Vh domains of an antibody each comprise SEQ ID NO:2.

* * * * *